US008591974B2

(12) United States Patent
Boghani et al.

(10) Patent No.: US 8,591,974 B2
(45) Date of Patent: *Nov. 26, 2013

(54) DELIVERY SYSTEM FOR TWO OR MORE ACTIVE COMPONENTS AS PART OF AN EDIBLE COMPOSITION

(75) Inventors: Navroz Boghani, Wharton, NJ (US); Petros Gebreselassie, Piscataway, NJ (US)

(73) Assignee: Kraft Foods Global Brands LLC, Northfield, IL (US)

( * ) Notice: Subject to any disclaimer, the term of this patent is extended or adjusted under 35 U.S.C. 154(b) by 1555 days.

This patent is subject to a terminal disclaimer.

(21) Appl. No.: 11/134,367

(22) Filed: May 23, 2005

(65) Prior Publication Data

US 2006/0034897 A1 Feb. 16, 2006

Related U.S. Application Data

(63) Continuation-in-part of application No. 10/719,298, filed on Nov. 21, 2003.

(51) Int. Cl.
A23G 4/18 (2006.01)
B65D 85/02 (2006.01)
A23L 1/00 (2006.01)

(52) U.S. Cl.
USPC ................................................ 426/89; 426/5

(58) Field of Classification Search
USPC ........................................................ 426/5, 89
See application file for complete search history.

(56) References Cited

U.S. PATENT DOCUMENTS

| | | | |
|---|---|---|---|
| 1,633,336 A | 6/1927 | Larson | |
| 1,936,456 A | 11/1933 | Larson | |
| 1,952,886 A * | 3/1934 | O'Brien | 106/429 |
| 2,191,199 A | 2/1940 | Hall | |
| 2,197,719 A | 4/1940 | Conner | |
| 2,876,167 A | 3/1959 | Manahan | |
| 2,866,446 A | 5/1959 | Kramer et al. | |
| 2,886,440 A | 5/1959 | Kramer et al. | |
| 2,886,441 A | 5/1959 | Kramer et al. | |
| 2,886,442 A | 5/1959 | Kramer et al. | |
| 2,886,443 A | 5/1959 | Rosenthal et al. | |
| 2,886,444 A | 5/1959 | Rosenthal et al. | |
| 2,886,445 A | 5/1959 | Rosenthal et al. | |
| 2,886,446 A | 5/1959 | Kramer et al. | |
| 2,886,449 A | 5/1959 | Rosenthal et al. | |
| 3,004,897 A | 10/1961 | Shore | |
| 3,052,552 A | 9/1962 | Koener et al. | |
| 3,117,027 A | 1/1964 | Lindlof et al. | |
| 3,124,459 A | 3/1964 | Erwin et al. | |
| 3,159,585 A | 12/1964 | Evans et al. | |
| 3,241,520 A | 3/1966 | Wurster et al. | |
| 3,341,416 A | 9/1967 | Anderson et al. | |
| 3,475,533 A | 10/1969 | Mayrand et al. | |
| 3,538,230 A | 11/1970 | Pader et al. | |
| 3,664,962 A | 5/1972 | Kelly et al. | |
| 3,664,963 A | 5/1972 | Pasin | |
| 3,677,771 A | 7/1972 | Kolar, Jr. | |
| 3,691,090 A | 9/1972 | Kitajima et al. | |
| 3,795,744 A | 3/1974 | Ogawa et al. | |
| 3,819,838 A | 6/1974 | Smith et al. | |
| 3,821,417 A | 6/1974 | Westall et al. | |
| 3,826,847 A | 7/1974 | Ogawa et al. | |
| 3,857,964 A | 12/1974 | Yolles | |
| 3,862,307 A | 1/1975 | Di Giulio | |
| 3,872,021 A | 3/1975 | McKnight | |
| 3,878,938 A | 4/1975 | Venables et al. | |
| 3,897,566 A | 7/1975 | Bahoshy et al. | |
| 3,912,817 A | 10/1975 | Sapsowitz | |
| 3,929,988 A | 12/1975 | Barth | |
| 3,930,026 A | 12/1975 | Clark | |
| 3,943,258 A | 3/1976 | Bahoshy et al. | |
| 3,962,416 A | 6/1976 | Katzen | |
| 3,962,463 A | 6/1976 | Witzel | |
| 3,974,293 A | 8/1976 | Witzel | |
| 3,984,574 A | 10/1976 | Comollo | |
| 4,032,661 A | 6/1977 | Rowsell et al. | |
| 4,033,994 A | 7/1977 | Watson et al. | |
| 4,037,000 A | 7/1977 | Burge et al. | |
| 4,045,581 A | 8/1977 | Mackay et al. | |
| 4,059,118 A | 11/1977 | Watson et al. | |
| 4,060,091 A | 11/1977 | Watson et al. | |
| 4,070,449 A | 1/1978 | Rowsell et al. | |
| 4,083,995 A | 4/1978 | Mitchell et al. | |
| 4,107,360 A | 8/1978 | Schmidgall | |
| 4,130,638 A | 12/1978 | Dhabhar et al. | |
| 4,136,163 A | 1/1979 | Watson et al. | |
| 4,139,639 A | 2/1979 | Bahoshy et al. | |
| 4,148,872 A | 4/1979 | Wagenknecht et al. | |
| 4,150,112 A | 4/1979 | Wagenknecht et al. | |
| 4,156,715 A | 5/1979 | Wagenknecht et al. | |
| 4,156,716 A | 5/1979 | Wagenknecht et al. | |
| 4,157,385 A | 6/1979 | Wagenknecht et al. | |
| 4,159,315 A | 6/1979 | Wagenknecht et al. | |
| 4,160,054 A | 7/1979 | Wagenknecht et al. | |
| 4,160,820 A | 7/1979 | Wagenknecht et al. | |
| 4,187,320 A | 2/1980 | Koch et al. | |
| 4,193,936 A | 3/1980 | Watson et al. | |
| 4,208,431 A | 6/1980 | Friello et al. | |
| 4,217,368 A | 8/1980 | Witzel et al. | |

(Continued)

FOREIGN PATENT DOCUMENTS

| | | |
|---|---|---|
| CA | 1208966 | 5/1986 |
| CA | 2238925 A1 | 11/1999 |

(Continued)

OTHER PUBLICATIONS

International Search Report as received in corresponding PCTUS06/06482 filed Feb. 24, 2006. (Jul. 21, 2006).

(Continued)

Primary Examiner — Daniel Sullivan
Assistant Examiner — Trevor Love
(74) Attorney, Agent, or Firm — Cantor Colburn LLP

(57) ABSTRACT

A delivery system for inclusion in an edible composition is formulated to have at least two active components with an encapsulating material for managing the release of the two actives relative to each other when used in an edible composition.

29 Claims, No Drawings

(56) References Cited

U.S. PATENT DOCUMENTS

| | | |
|---|---|---|
| 4,224,345 A | 9/1980 | Tezuka et al. |
| 4,230,688 A | 10/1980 | Rowsell et al. |
| 4,271,197 A | 6/1981 | Hopkins et al. |
| 4,271,199 A | 6/1981 | Cherukuri et al. |
| 4,276,312 A | 6/1981 | Merritt |
| 4,295,845 A | 10/1981 | Sepulveda et al. |
| 4,314,990 A | 2/1982 | Denny, Jr. et al. |
| 4,340,583 A | 7/1982 | Wason |
| 4,352,822 A | 10/1982 | Cherukuri et al. |
| 4,352,823 A | 10/1982 | Cherukuri et al. |
| 4,352,825 A | 10/1982 | Cherukuri et al. |
| 4,363,756 A | 12/1982 | Sepulveda et al. |
| 4,370,350 A | 1/1983 | Fisher et al. |
| 4,384,004 A | 5/1983 | Cea et al. |
| 4,386,106 A | 5/1983 | Merritt et al. |
| 4,388,328 A | 6/1983 | Glass |
| 4,452,821 A | 6/1984 | Gergely |
| 4,457,857 A | 7/1984 | Sepulveda et al. |
| 4,459,425 A | 7/1984 | Amano et al. |
| 4,485,118 A | 11/1984 | Carroll et al. |
| 4,497,832 A | 2/1985 | Cherukuri et al. |
| 4,513,012 A | 4/1985 | Carroll et al. |
| 4,515,769 A | 5/1985 | Merritt et al. |
| 4,518,615 A | 5/1985 | Cherukuri et al. |
| 4,568,560 A | 2/1986 | Schobel |
| 4,585,649 A | 4/1986 | Lynch |
| 4,590,075 A | 5/1986 | Wei et al. |
| 4,597,970 A | 7/1986 | Sharma et al. |
| 4,614,649 A | 9/1986 | Gorman et al. |
| 4,616,654 A | 10/1986 | Bacchelli |
| 4,627,987 A | 12/1986 | Barnett et al. |
| 4,634,593 A | 1/1987 | Stroz et al. |
| 4,663,152 A | 5/1987 | Barth et al. |
| 4,673,577 A | 6/1987 | Patel |
| 4,711,784 A | 12/1987 | Yang |
| 4,722,845 A | 2/1988 | Cherukuri et al. |
| 4,726,953 A | 2/1988 | Carroll et al. |
| 4,740,376 A | 4/1988 | Yang |
| 4,741,905 A | 5/1988 | Huzinec |
| 4,749,575 A | 6/1988 | Rotman |
| 4,751,095 A | 6/1988 | Karl et al. |
| 4,752,481 A | 6/1988 | Dokuzovic |
| 4,753,790 A | 6/1988 | Silva et al. |
| 4,764,382 A | 8/1988 | Kydonieus et al. |
| 4,771,784 A | 9/1988 | Kozin et al. |
| 4,786,502 A | 11/1988 | Chapura et al. |
| 4,800,087 A | 1/1989 | Mehta |
| 4,803,082 A | 2/1989 | Cherukuri et al. |
| 4,804,548 A | 2/1989 | Sharma et al. |
| 4,816,265 A | 3/1989 | Cherukuri et al. |
| 4,822,599 A | 4/1989 | Mitra |
| 4,824,681 A | 4/1989 | Schobel et al. |
| 4,828,845 A | 5/1989 | Zamudio-Tena et al. |
| 4,828,857 A | 5/1989 | Sharma et al. |
| 4,842,762 A | 6/1989 | Sabol, Jr. et al. |
| 4,863,745 A | 9/1989 | Zibell |
| 4,871,570 A | 10/1989 | Barnett et al. |
| 4,904,482 A | 2/1990 | Patel et al. |
| 4,911,934 A | 3/1990 | Yang et al. |
| 4,915,958 A | 4/1990 | Faust et al. |
| 4,918,182 A | 4/1990 | Jackson et al. |
| 4,919,841 A | 4/1990 | Kamel et al. |
| 4,923,684 A | 5/1990 | Ibrahim et al. |
| 4,927,646 A | 5/1990 | Jenner et al. |
| 4,929,447 A | 5/1990 | Yang |
| 4,931,293 A | 6/1990 | Cherukuri et al. |
| 4,933,190 A | 6/1990 | Cherukuri et al. |
| 4,940,588 A | 7/1990 | Sparks et al. |
| 4,952,402 A | 8/1990 | Sparks et al. |
| 4,952,407 A | 8/1990 | Record et al. |
| 4,954,353 A | 9/1990 | Cherukuri et al. |
| 4,971,797 A | 11/1990 | Cherukuri et al. |
| 4,971,806 A | 11/1990 | Cherukuri et al. |
| 4,978,537 A | 12/1990 | Song |
| 4,981,698 A | 1/1991 | Cherukuri et al. |
| 4,985,236 A | 1/1991 | Ibrahim et al. |
| 4,986,991 A | 1/1991 | Yatka et al. |
| 4,997,659 A | 3/1991 | Yatka et al. |
| 5,000,965 A * | 3/1991 | Killeen et al. .................... 426/5 |
| 5,004,595 A | 4/1991 | Cherukuri et al. |
| 5,009,893 A | 4/1991 | Cherukuri et al. |
| 5,009,900 A | 4/1991 | Levine et al. |
| 5,017,385 A | 5/1991 | Wienecke |
| 5,035,882 A | 7/1991 | Hussein et al. |
| 5,041,294 A | 8/1991 | Patel |
| 5,043,154 A | 8/1991 | Gaffar et al. |
| 5,043,169 A | 8/1991 | Cherukuri et al. |
| 5,057,327 A | 10/1991 | Yatka et al. |
| 5,057,328 A | 10/1991 | Cherukuri et al. |
| 5,059,429 A | 10/1991 | Cherukuri et al. |
| 5,064,658 A | 11/1991 | Cherukuri et al. |
| 5,073,389 A | 12/1991 | Wienecke |
| 5,080,877 A | 1/1992 | Chane-Ching et al. |
| 5,082,671 A | 1/1992 | Cherukuri |
| 5,084,278 A | 1/1992 | Mehta |
| 5,096,699 A | 3/1992 | Gaffar et al. |
| 5,096,701 A | 3/1992 | White, Jr. et al. |
| 5,100,678 A | 3/1992 | Reed et al. |
| 5,108,763 A | 4/1992 | Chau et al. |
| 5,126,151 A | 6/1992 | Bodor et al. |
| 5,139,793 A | 8/1992 | Johnson et al. |
| 5,139,794 A | 8/1992 | Patel et al. |
| 5,139,798 A | 8/1992 | Yatka et al. |
| 5,154,939 A | 10/1992 | Broderick et al. |
| 5,158,790 A | 10/1992 | Witkewitz et al. |
| 5,164,210 A | 11/1992 | Campbell et al. |
| 5,169,657 A | 12/1992 | Yatka et al. |
| 5,169,658 A | 12/1992 | Yatka et al. |
| 5,174,514 A | 12/1992 | Prodi |
| 5,176,900 A | 1/1993 | White, Jr. et al. |
| 5,198,251 A | 3/1993 | Song et al. |
| 5,202,112 A | 4/1993 | Prencipe et al. |
| 5,208,009 A | 5/1993 | Gaffar et al. |
| 5,226,335 A | 7/1993 | Sitte et al. |
| 5,227,154 A | 7/1993 | Reynolds |
| 5,227,182 A | 7/1993 | Song et al. |
| 5,229,148 A | 7/1993 | Copper |
| 5,240,710 A | 8/1993 | Bar-Shalom et al. |
| 5,244,670 A | 9/1993 | Upson et al. |
| 5,256,402 A | 10/1993 | Prencipe et al. |
| 5,266,335 A | 11/1993 | Cherukuri et al. |
| 5,266,592 A | 11/1993 | Grub et al. |
| 5,273,741 A | 12/1993 | Gaftar et al. |
| 5,284,659 A | 2/1994 | Cherukuri et al. |
| 5,300,283 A | 4/1994 | Prencipe et al. |
| 5,300,305 A | 4/1994 | Stapler et al. |
| 5,334,375 A | 8/1994 | Nabi et al. |
| 5,334,396 A | 8/1994 | Yatka |
| 5,336,509 A | 8/1994 | McGrew et al. |
| 5,352,439 A | 10/1994 | Norfleet et al. |
| 5,364,627 A | 11/1994 | Song |
| 5,372,824 A | 12/1994 | Record et al. |
| 5,380,530 A | 1/1995 | Hill |
| 5,385,729 A | 1/1995 | Prencipe et al. |
| 5,391,315 A | 2/1995 | Ashkin |
| 5,405,604 A | 4/1995 | Hall |
| 5,407,665 A | 4/1995 | McLaughlin et al. |
| 5,413,799 A | 5/1995 | Song et al. |
| 5,415,880 A | 5/1995 | Song et al. |
| 5,429,827 A | 7/1995 | Song et al. |
| 5,431,930 A | 7/1995 | Patel et al. |
| 5,437,876 A | 8/1995 | Synosky et al. |
| 5,437,878 A | 8/1995 | Panhorst et al. |
| 5,451,404 A | 9/1995 | Furman |
| 5,458,879 A | 10/1995 | Singh et al. |
| 5,462,754 A | 10/1995 | Synosky et al. |
| 5,474,787 A | 12/1995 | Grey et al. |
| 5,480,668 A | 1/1996 | Nofre et al. |
| 5,487,902 A | 1/1996 | Andersen et al. |
| 5,494,689 A | 2/1996 | Lee et al. |
| 5,498,378 A | 3/1996 | Tsaur et al. |
| 5,501,864 A | 3/1996 | Song et al. |
| 5,503,823 A | 4/1996 | Norfleet et al. |
| 5,505,933 A | 4/1996 | Norfleet et al. |

(56) References Cited

U.S. PATENT DOCUMENTS

| | | |
|---|---|---|
| 5,523,098 A | 6/1996 | Synosky et al. |
| 5,532,004 A | 7/1996 | Bell et al. |
| 5,545,424 A | 8/1996 | Nakatsu et al. |
| 5,582,816 A | 12/1996 | Mandanas et al. |
| 5,589,160 A | 12/1996 | Rice |
| 5,589,194 A | 12/1996 | Tsuei et al. |
| 5,599,527 A | 2/1997 | Hsu et al. |
| 5,603,920 A | 2/1997 | Rice |
| 5,603,971 A | 2/1997 | Porzio et al. |
| 5,618,517 A | 4/1997 | Miskewitz |
| 5,626,892 A | 5/1997 | Kehoe et al. |
| 5,629,035 A | 5/1997 | Miskewitz |
| 5,633,027 A | 5/1997 | Cherukuri et al. |
| 5,637,618 A | 6/1997 | Kurtz et al. |
| 5,645,821 A | 7/1997 | Libin |
| 5,651,958 A | 7/1997 | Rice |
| 5,658,553 A | 8/1997 | Rice |
| 5,676,932 A | 10/1997 | Wason et al. |
| 5,693,334 A | 12/1997 | Miskewitz |
| 5,698,215 A | 12/1997 | Kalili et al. |
| 5,702,687 A | 12/1997 | Miskewitz |
| 5,713,738 A | 2/1998 | Yarborough |
| 5,716,601 A | 2/1998 | Rice |
| 5,725,865 A | 3/1998 | Mane et al. |
| 5,736,175 A | 4/1998 | Cea et al. |
| 5,744,180 A | 4/1998 | Cherukuri et al. |
| 5,756,074 A | 5/1998 | Ascione et al. |
| 5,783,725 A | 7/1998 | Kuhn et al. |
| 5,789,002 A | 8/1998 | Duggan et al. |
| 5,800,848 A | 9/1998 | Yatka et al. |
| 5,824,291 A | 10/1998 | Howard |
| 5,853,758 A | 12/1998 | Lo |
| 5,869,028 A | 2/1999 | McGill et al. |
| 5,879,728 A | 3/1999 | Graff et al. |
| 5,912,007 A | 6/1999 | Pan et al. |
| 5,939,051 A | 8/1999 | Santalucia et al. |
| 5,942,211 A | 8/1999 | Harper et al. |
| 6,027,746 A | 2/2000 | Lech |
| 6,056,992 A | 5/2000 | Lew |
| 6,159,509 A | 12/2000 | Johnson et al. |
| 6,174,514 B1 | 1/2001 | Cherukuri et al. |
| 6,190,591 B1 | 2/2001 | van Lengerich |
| 6,190,644 B1 | 2/2001 | McClanahan et al. |
| 6,239,690 B1 | 5/2001 | Burbidge et al. |
| 6,261,540 B1 | 7/2001 | Nelson |
| 6,290,933 B1 | 9/2001 | Durga et al. |
| 6,306,429 B1 | 10/2001 | Bealin-Kelly |
| 6,365,209 B2 | 4/2002 | Cherukuri |
| 6,379,654 B1 | 4/2002 | Gebreselassie et al. |
| 6,413,573 B1 | 7/2002 | Reichart et al. |
| 6,416,744 B1 | 7/2002 | Robinson et al. |
| 6,428,827 B1 | 8/2002 | Song et al. |
| 6,436,461 B1 | 8/2002 | Bouwmeesters et al. |
| 6,471,945 B2 | 10/2002 | Luo et al. |
| 6,475,469 B1 | 11/2002 | Montgomery |
| 6,479,071 B2 | 11/2002 | Holme et al. |
| 6,485,739 B2 | 11/2002 | Luo et al. |
| 6,506,366 B1 | 1/2003 | Leinen et al. |
| 6,534,091 B1 | 3/2003 | Garces Garces et al. |
| 6,537,595 B1 | 3/2003 | Hyodo et al. |
| 6,555,093 B2 | 4/2003 | Alvarez Hernandez |
| 6,555,145 B1 | 4/2003 | Cherukuri |
| 6,599,542 B1 | 7/2003 | Abdel-Malik et al. |
| 6,623,266 B2 | 9/2003 | Jani et al. |
| 6,627,233 B1 | 9/2003 | Wolf et al. |
| 6,673,844 B2 | 1/2004 | Kumamoto et al. |
| 6,685,916 B1 | 2/2004 | Holme et al. |
| 6,692,778 B2 | 2/2004 | Yatka et al. |
| 6,696,044 B2 | 2/2004 | Luo et al. |
| 6,717,167 B2 | 4/2004 | Noda |
| 6,759,066 B2 | 7/2004 | Schnell et al. |
| 6,780,443 B1 | 8/2004 | Nakatsu et al. |
| 6,838,106 B2 | 1/2005 | Kumamoto et al. |
| 6,974,597 B2 | 12/2005 | Ohta et al. |
| 6,998,144 B2 | 2/2006 | Merkel et al. |
| 7,022,352 B2 | 4/2006 | Castro et al. |
| 7,025,999 B2 | 4/2006 | Johnson et al. |
| 7,189,760 B2 | 3/2007 | Erman et al. |
| 7,507,427 B2 | 3/2009 | Andersen et al. |
| 7,585,516 B2 | 9/2009 | Pacetti |
| 7,850,990 B2 | 12/2010 | Tardi et al. |
| 2001/0008635 A1 | 7/2001 | Quellet et al. |
| 2001/0021404 A1 | 9/2001 | Uhlemann et al. |
| 2002/0044968 A1 | 4/2002 | Van Lengerich |
| 2002/0122842 A1 | 9/2002 | Seielstad et al. |
| 2002/0150616 A1 | 10/2002 | Vandecruys |
| 2003/0004215 A1 | 1/2003 | Van Laere et al. |
| 2003/0077362 A1 | 4/2003 | Panhorst et al. |
| 2003/0099740 A1 | 5/2003 | Colle et al. |
| 2003/0113274 A1 | 6/2003 | Holme et al. |
| 2003/0236183 A1 | 12/2003 | De Bruijn et al. |
| 2004/0136928 A1 | 7/2004 | Holme et al. |
| 2004/0175489 A1 | 9/2004 | Clark et al. |
| 2005/0019445 A1 | 1/2005 | Wolf et al. |
| 2005/0025721 A1 | 2/2005 | Holme et al. |
| 2005/0112236 A1 | 5/2005 | Boghani et al. |
| 2005/0196503 A1 | 9/2005 | Srivastava |
| 2005/0196517 A1 | 9/2005 | Hodanko et al. |
| 2005/0202143 A1 | 9/2005 | Roy et al. |
| 2005/0208084 A1 | 9/2005 | Ley et al. |
| 2005/0210306 A1 | 9/2005 | Rich et al. |
| 2005/0214348 A1 | 9/2005 | Boghani et al. |
| 2005/0220867 A1 | 10/2005 | Boghani et al. |
| 2005/0260266 A1 | 11/2005 | Gebreselassie et al. |
| 2006/0034897 A1 | 2/2006 | Boghani et al. |
| 2006/0068057 A1 | 3/2006 | Boghani et al. |
| 2006/0068059 A1 | 3/2006 | Boghani et al. |
| 2006/0177383 A1 | 8/2006 | Gebreselassie et al. |
| 2006/0251768 A1 | 11/2006 | Bouquerand |
| 2006/0263474 A1 | 11/2006 | Luo |
| 2007/0036733 A1 | 2/2007 | Spence et al. |
| 2007/0048424 A1 | 3/2007 | Moza et al. |
| 2008/0063747 A1 | 3/2008 | Boghani et al. |
| 2008/0160138 A1 | 7/2008 | Boghani et al. |
| 2008/0166449 A1 | 7/2008 | Kabse et al. |
| 2008/0187621 A1 | 8/2008 | Boghani et al. |
| 2008/0199564 A1 | 8/2008 | Boghani et al. |
| 2009/0022846 A1 | 1/2009 | Wittorff et al. |
| 2009/0074911 A1 | 3/2009 | Boghani et al. |
| 2009/0089167 A1 | 4/2009 | Boghani et al. |
| 2009/0098252 A1 | 4/2009 | Boghani et al. |
| 2009/0130250 A1 | 5/2009 | Andersen et al. |
| 2009/0162418 A1 | 6/2009 | Boghani et al. |
| 2009/0175982 A1 | 7/2009 | Boghani et al. |
| 2009/0220642 A1 | 9/2009 | Boghani et al. |

FOREIGN PATENT DOCUMENTS

| | | |
|---|---|---|
| EP | 0 067 595 | 12/1982 |
| EP | 0 252 374 | 1/1988 |
| EP | 0 255 260 | 2/1988 |
| EP | 0 273 009 | 6/1988 |
| EP | 0 434 321 | 6/1991 |
| EP | 0 453 397 | 10/1991 |
| GB | 875763 | 8/1961 |
| GB | 1351761 | 1/1972 |
| GB | 1444024 | 7/1996 |
| JP | 63-245638 | 10/1988 |
| JP | 63-273947 | 10/1988 |
| JP | 02083030 | 3/1990 |
| JP | 2623769 | 6/1997 |
| JP | 9/309822 | 12/1997 |
| JP | 10-512862 | 12/1998 |
| WO | 8503414 | 8/1985 |
| WO | 88/00463 | 1/1988 |
| WO | 98/29088 | 7/1988 |
| WO | 89/03170 | 4/1989 |
| WO | 8911212 | 11/1989 |
| WO | 9004926 | 5/1990 |
| WO | 9013994 | 11/1990 |
| WO | 91/07104 | 5/1991 |
| WO | 9107104 | 5/1991 |
| WO | 9202145 | 2/1992 |
| WO | 92/06160 | 4/1992 |

(56) References Cited

FOREIGN PATENT DOCUMENTS

| | | |
|---|---|---|
| WO | 9322939 | 11/1993 |
| WO | 9507683 | 3/1995 |
| WO | 9511671 | 5/1995 |
| WO | 95/33034 | 12/1995 |
| WO | 96/19193 | 6/1996 |
| WO | 9617524 | 6/1996 |
| WO | 9620608 | 7/1996 |
| WO | WO 96/20608 * | 7/1996 |
| WO | WO 96/22080 | 7/1996 |
| WO | 97/02009 | 1/1997 |
| WO | 97/02011 | 1/1997 |
| WO | 9702273 | 1/1997 |
| WO | 9706695 | 2/1997 |
| WO | 9724036 | 7/1997 |
| WO | 98/03076 | 1/1998 |
| WO | 98/18339 | 5/1998 |
| WO | 98/23165 | 6/1998 |
| WO | 9913870 | 3/1999 |
| WO | 9915032 | 4/1999 |
| WO | 98/27798 | 6/1999 |
| WO | 9927798 | 6/1999 |
| WO | 99/43294 | 9/1999 |
| WO | 99/62354 | 12/1999 |
| WO | 0001253 | 1/2000 |
| WO | 00/35296 | 6/2000 |
| WO | 00/35298 | 6/2000 |
| WO | 00/36924 | 6/2000 |
| WO | 0069282 | 11/2000 |
| WO | 00/75274 | 12/2000 |
| WO | 01/76384 | 10/2001 |
| WO | 0191571 A2 | 12/2001 |
| WO | 02/47489 | 6/2002 |
| WO | 02/055649 | 7/2002 |
| WO | 03020047 A1 | 3/2003 |
| WO | 03063604 A1 | 8/2003 |
| WO | 2004006967 A1 | 1/2004 |
| WO | WO 2004/010998 | 2/2004 |
| WO | 2004064544 A1 | 8/2004 |
| WO | 2004077956 A2 | 9/2004 |
| WO | 2005016022 A1 | 2/2005 |
| WO | 2005/051427 | 6/2005 |
| WO | 2006079056 A1 | 7/2006 |
| WO | 2006089200 A2 | 8/2006 |

OTHER PUBLICATIONS

U.S. Appl. No. 12/577,986, filed Oct. 13, 2009, Boghani, et al.
"Caprol® 3GO CAS No. 9007-48-1" XP002401201. Retrieved from the Internet: URL: http://www.abietccorp.com/documents/3go-17_000.pdf> [retrieved on Sep. 28, 2006].

The State Intellectual Property Office of P.R. China, Application No. 2006800096900, Applicant: Cadbury Adams USA LLC, Title of Invention: Controlled Release Oral Delivery Systems, Notification of the First Office Action, Date: Feb. 5, 2010, 10 pages.
DE19653100 A1, Jul. 23, 1998, Abstract Only, 1 page.
Demmers et al., "Effect of Surfacants and Proteolytic Enzymes on Artificial Calculus Formation", Surfacents and Enzymes, Calculus, Aug. 1867, pp. 28-30.
Emulsifiers with HLB Vlaues, Last Accessed Sep. 27, 2011, pp. 1-3, http://www.theherbarie.com/files/resource-center/formulating/Emulsifiers_HLB_Values.pdf.
European Patent Office, Application No. 06 717 548.9 1221; Ref. MG/P/85286, EP Office Communication dated: May 3, 2010, 4 pages.
ES2080703 A1, Feb. 1, 1996, Abstract Only, 1 page.
Gantrez® AN; ISP Polymers for Oral Care; Products and Properties, last downloaded from http://www.ispcorp.com/products/oralcare/content/brochure/oral/prod.html on Jun. 9, 2004, 5 pages.
Hercules Incorporated, Technical Information Bulletin VC-566C, 2000, 6 pages.
"HLB Systems" [Online] pp. 1-4, XP002401202. Retrieved from the Internet: URL: http://pharmcal.tripod.com/ch17.htm. [retrieved on Sep. 28, 2006].
JP01206969, Aug. 21, 1989, Abstract Only, 1 page.
JP02227044, Sep. 10, 1990, Abstract Only, 1 page.
JP6079165 A, Mar. 22, 1994, Abstract Only, 1 page.
JP8308500 A, Nov. 26, 1996, Abstract Only, 1 page.
Leffingwell, John C., "Cool without Menthol & Cooler than menthol and Cooling compounds as Insect Repellents" From the Internet: URL: http://www.leffingwell.com/cooler_than_menthol.htm [updated Apr. 5, 2006].
McClements, "Food Emulsions, Principles, Practices, and Techniques", 2005, Contemporary Food Science, 2nd Edition, Title pages and p. 132, 3 pages.
Ottinger et al., "Quantitative Modle Studies on the Efficiency of Precursors in the Formation of Cooling-Active 1-Pyrrolidinyl-2-cyclopenten-1-ones and Bitter-Tasting Cyclopenta-[b]azepin-8(1H)-ones", Journal of Agricultural and Food Chemistry; 2002; pp. 5156-5161.
Ovejero-Lopez et al., "Flavor Release Measurement from Gum Model System", J. Argic. Food Chem. 52, 2004, pp. 8119-8126.
Parikh et al., "Tensile Properties of Free Fillms Cast from Aqueous Ethylcellulose Dispersions", Pharmaceutical Research, vol. 10, No. 6, 1993, pp. 810-815.
Prencipe et al., "Squeezing out a better toothpaste", ChemTech., 1999, 7 pages.
Rassing, "Chewing gum as a drug delivery system", Advanced Drug Delivery Reviews, vol. 13, 1994, pp. 89-121.

* cited by examiner

DELIVERY SYSTEM FOR TWO OR MORE ACTIVE COMPONENTS AS PART OF AN EDIBLE COMPOSITION

CROSS-REFERENCE TO RELATED APPLICATIONS

The present application is a continuation-in-part of U.S. application Ser. No. 10/719,298 filed Nov. 21, 2003, pending.

BACKGROUND OF THE INVENTION

1. Field of the Invention

A delivery system for inclusion in an edible composition is formulated to have at least two active components with an encapsulating material for managing the release of the two actives relative to each other when used in an edible composition.

2. Description of the Background

High intensity sweeteners generally have a sweetening intensity greater than sugar (sucrose) and a caloric value lower than that of sugar at equivalent sweetness levels. In some situations, it is especially desirable to control the release of high intensity sweeteners in compositions since the high sweetness levels can easily overwhelm the consumer. Moreover, the controlled release of the sweetener provides desirable masking of unpleasant tasting materials and may help bring out flavor characteristics of other ingredients. Because each high intensity sweetener is chemically and physically distinct, each is a challenge to use in an edible composition and each exhibits one or more shortcomings, which may be moderated by encapsulation.

For example, many high intensity sweeteners lose their sweetness intensity rapidly when used in edible compositions such as chewing gums and confections with certain flavors. Encapsulation can modulate and prolong release to provide a more desirable taste profile. Some high intensity sweeteners such as saccharin, stevioside, acesulfame-K, glycyrrhizin, and thaumatin have an associated bitter taste or off-note. Certain high intensity sweeteners are also unstable in the presence of certain chemicals including aldehydes and ketones, and sensitive to exposure to environmental conditions including moisture. Solid sucralose is known to turn dark during prolonged storage and/or upon exposure to heat and ambient air. Encapsulation can be used to isolate unstable compounds to prevent degradation and prolong shelf life.

Typically, the taste profile of a high intensity sweetener can be described as a rapid burst of sweetness. Usually, high intensity sweeteners reach their peak sweet taste rapidly, with the intensity of sweet taste rapidly declining soon thereafter. The initial rapid burst can be unpleasant to many consumers as the strong sweet taste tends to overpower the other flavors that may be present in the edible composition. The relatively rapid loss of sweetness can also result in a bitter aftertaste. For this reason, it may be desirable to encapsulate high intensity sweeteners with an encapsulating material in order to modulate and prolong the release and to chemically stabilize and enhance the overall taste profile.

By incorporating different active components into separate delivery systems and then mixing the separate delivery systems in a single edible composition, different release profiles may be obtained due to the different interaction of the active component with the encapsulating material. The Inventors have identified this as a problem when trying to control the relative release profiles of the actives in a single edible composition.

SUMMARY OF THE INVENTION

The present invention is a significant advance in the art by providing a delivery system that provides controlled and/or delayed release of two or more active agents at a more controlled and/or consistent rate relative to the situation where the two or more active agents are incorporated into separate delivery systems. In further embodiments, the amount of the two or more active components may be adjusted to provide a consistent controlled and/or delayed release profile of the two or more active components.

By combining the two or more active agents into a single delivery system, the delivery of the two or more active agents when incorporated into an edible composition and consumed, provides a way to control the release profiles of these active agents relative to each other when compared to formulating an edible composition with the same active agents in separate delivery systems.

DETAILED DESCRIPTION OF THE INVENTION

In one aspect of the present invention, there is provided a delivery system for inclusion in an edible composition such as a chewing gum composition or confectionery composition having at least two active components with encapsulating material.

In a further aspect of the present invention there is provided an edible composition such as a chewing gum composition or a confectionery composition comprising at least one edible composition-forming component and such a delivery system.

In a still further aspect of the invention there is provided a method of preparing a target delivery system for an edible composition comprising combining at least two active components, at least one encapsulating material, and optionally at least one additive until a preselected and/or desired target delivery system based on the criteria described herein is obtained based on comparison with at least one sample delivery system having the same or similar active components and a known release profile of the active component.

There is also provided a method of preparing a target delivery system for an edible composition useful for delivering at least two active components at a desired release profile, said method comprising encapsulating the at least two active components in an encapsulating material in a manner that provides the target delivery system with the preselected and/or desired characteristics as described herein.

In addition, a method is provided for preparing an edible composition containing at least one delivery system useful for delivering at least two active components at a desired release profile by mixing the at least two active components with an encapsulating material in a manner that provides the target delivery system with the preselected and/or desired characteristics as described herein associated with the desired release rate and/or release profile enabling the delivery system to release the at least two active components from the edible composition at desired release profile, and adding the target delivery system to the edible composition.

There is also provided edible compositions containing the delivery system described herein. Although one embodiment of the present invention relates to chewing gum compositions, confectionery compositions and beverages, the present invention can be utilized to produce a variety of edible compositions including, but not limited to, food products, foodstuffs, nutrient-containing compositions, pharmaceuticals, nutraceuticals, vitamins and other products that may be prepared for consumption by the consumer. As used herein, chewing gum compositions include bubble gum compositions.

Because the delivery system may be readily incorporated into an edible composition, the edible compositions which may benefit from and are encompassed by the present invention are wide ranging as indicated above.

The term "delivery system" as used herein is meant to encompass the at least one encapsulating material with at least two active components as well as other optional additives used to form the delivery system as hereinafter described. It will be understood that the edible compositions of the present invention may contain a plurality of delivery systems with each delivery system containing a single or multiple combinations of active components. In addition, delivery systems containing only one active and/or free (non-encapsulated) active components may also be added to the edible composition.

The term "encapsulating material" is meant to encompass any one or more edible water insoluble or soluble materials capable of forming a solid coating or film as a protective barrier around the active component. As understood from the description provided herein, the encapsulating material forms a matrix with the at least one active component whereby the encapsulating material can completely encapsulate at least one active component, can partially encapsulate the at least one active component, or can associate with the at least one active component whereby the encapsulating material provides controlled and/or delayed release of the at least one active component in accordance with the description herein.

An ingredient in an edible composition will have a release profile when a consumer consumes the edible composition. In some embodiments, the ingredient may be released by mechanical action of chewing, and/or by chemical action or reaction of the ingredient with another ingredient or saliva or other material in the consumer's mouth. The release profile for the ingredient is indicative of the availability of the ingredient in the consumer's mouth to interact with receptors (e.g., taste receptors), mucous membranes, teeth, etc. in the consumer's mouth. An edible composition may include the same or different release profiles for different ingredients. In some embodiments, the release profile for only a finite number (e.g., one or two) ingredients may be of primary importance.

The release profile of an ingredient in an edible composition can be influenced by many factors such as, for example, rate of chewing, intensity of chewing, the amount of the ingredient, how the form of the ingredient added to the edible composition (e.g., encapsulated in a delivery system, unencapsulated, pretreated), the edible composition is mixed or otherwise prepared, when or how the ingredient is added to other ingredients in the edible composition, the ratio of the amount of the ingredient to the amount of one or more other ingredients in the edible composition, the ratio of the amount of the ingredient to the amount of one or more other ingredients in a delivery system that is included in the edible composition, etc.

In some embodiments, a release profile for an ingredient may be relate to a specific time period. For example, release of an ingredient from a delivery system may increase during a first time period, reach a peak, and then decrease during a second time period. Thus, in some embodiments, a release profile for an ingredient may include one or more time periods, each of which has an associated release rate (which may or may not be known or measurable). The time periods may be the same length of time or may be different lengths of time. A first time period may have a fixed or varied release rate for the ingredient during the first time period and an average release rate for the ingredient over the first time period. Similarly, a second time period may have a fixed or varied release rate for the ingredient during the second time period and an average release rate for the ingredient over the second time period. In some embodiments, a release profile for an ingredient in an edible composition may include only one time period or be related to only a single point in time, both of which typically relate or are relative to when consumption of the edible composition has started. In other embodiments, a release profile may relate to two or more time periods and/or two or more points in time, all of which typically relate or are relative to when consumption of the edible product has started.

In some embodiments, a release profile may be defined or characterized by one or more factors or characteristics, even if other or all aspects of the release profile are not determined, selected, or even known. Thus, in some embodiments, a release profile for an ingredient may include only one characteristic. For example, characteristics may include one or more of the following: release rate of an ingredient during a time period, a specific time period during which a minimum, average, or predominant amount of an ingredient is released during consumption of an edible composition that includes the ingredient (even if some of the ingredient is released before or after the specific time period and even if the release rate during the time period is not specified or varies), a specific time after which a minimum, average, or predominant amount if an ingredient is released during consumption of an edible composition that includes the ingredient (even if some of the ingredient is released before the specific time and even if the release rates are or are not specified), etc.

In some embodiments, managing a release profile for one or more ingredients may include changing or otherwise managing the starting and ending times for the time periods, changing or otherwise managing the lengths of the time periods, and/or changing or otherwise managing the release rates during the time periods. For example, managing a release profile may include changing or managing a release rate during a time period. An ingredient can be released more quickly or earlier during a first or second time period by increasing its release rate during these time periods. Likewise, the ingredient can be released more slowly or in a more delayed manner during the first or second time periods by decreasing its release rate during these time periods. As another example, managing a release profile may include shifting the start and end of the time periods in the release profile, but the length of the time periods may stay the same and the release rates of the ingredient(s) during the time periods may stay the same (e.g., the release of an ingredient may be managed to delay the release of the predominant amount of the ingredient by one minute, five minutes, ten minutes, thirty minutes, etc.). As a third example, managing a release profile may include shifting the start or end of one or more time periods and changing the release rate within the one or more time periods.

In some embodiments, causing a delay in a release of an ingredient in an edible composition includes causing a delay in the release or availability of the predominant of the ingredient after consumption of the edible product begins and/or causing release or availability of a desire, predominant, or minimum amount of the ingredient at a certain time, after a certain time, or during a desired time period after consumption of the edible composition begins. In some embodiments, none of the ingredient will be released or become available before the certain time or before or after the desired time period. In other embodiments, some of the ingredient may be released or become available before the certain time and/or before or after the desired time period.

In some embodiments, determining or selecting a desired release profile may include determining or selecting one or more factors or characteristics of the desired release profile, as previously described above. The factors or characteristics then serve to define or characterize the release profile, even if other or all aspects of the release profile are not determined or selected. Thus, determining or selecting a release profile for an ingredient can includes situations where only one characteristic for the release of the ingredient is determined or selected. In some embodiments, characteristic may be determined or measured by one or more techniques or methods such as, for example, chemical and/or mechanical testing and analysis, consumer testing, descriptive or expert taste or chew panel, other in vivo or in vitro testing, etc.

The present invention is directed generally to a delivery system as defined herein for use in edible compositions, which comprises an encapsulating material and active components. The delivery system of the present invention is formulated to provide consistent controlled release of the active components over a preselected period of time, such as an extended period of time, particularly relative to the release of the two or more active components separately incorporated in delivery systems over this same period of time. This period of time may vary depending on the type of product in which the delivery system is incorporated, the type of encapsulating material, the type of active, other ingredients (e.g. fats) in the product, etc. One of skill in the art, based on the disclosure herein can adjust the delivery system to achieve the desired effect.

An extended period of time as used herein, relates to an increased release of the active ingredients from the delivery system for over a greater period of time than previously described systems and can be at least 15 minutes, including at least 20 minutes, at least 25 minutes, at least 30 minutes, as well as all values and ranges there between, for example, about 25 to 30 minutes, 45 to 60 minutes or more. Furthermore, the delivery system of the present invention also provides a way to not only deliver active agents over a prolonged period of time but also maintain an increased intensity of the active ingredients over the extended period of time. For example, if the active ingredient is a flavor or sweetener then in one aspect of the invention, the amount of active agents released can vary during the extended period of time. For example, at an early stage of delivery the amount of active components released (based on the total amount present in the delivery system at that time) can be greater than the amount of active components released during subsequent or later periods (based on the total amount present in the delivery system at that time).

In one embodiment, the extended period of time results in retaining at least about 5% of the at least two active components after 30 minutes from the start of delivering the active component in the edible composition, such as the start of chewing a chewing gum composition, including at least about 10%, 15%, 20%, 25%, 30%, or more after 30 minutes. In another embodiment, the extended period of time results in retaining at least about 10% of the at least two active components after 20 minutes from the start of delivering the active component, including at least about 15%, 20%, 25%, 30%, 40%, 50% or more after 20 minutes. In another embodiment, the extended period of time results in retaining at least about 30% of the at least two active components after 15 minutes from the start of delivering the active component, including at least about 30%, 40%, 50%, 60%, 70%, 75% or more after 15 minutes.

In another embodiment, using sweeteners in chewing gum as an example, the extended period of time results in a perceived sweetness intensity during at least the entire period of time noted above, e.g., at least about 15 minutes, at least about 20 minutes, at least about 30 minutes, etcetera from the start of chewing the chewing gum composition. Moreover, extending the period of time that the sweeteners are available during chewing may extend the amount of time that flavor is perceived by the consumer.

The delivery system facilitates the controlled release of the active components in a wide variety of edible compositions including chewing gum compositions, food products, confectionery compositions, pharmaceutical compositions, beverages, foodstuffs, nutrient-containing compositions, vitamins, nutraceuticals and the like.

The delivery system is developed in accordance with the present invention may be selected, depending in part on the active components and the release rate and/or profiles of the desired active components, from a standard of known delivery systems containing the active components at known release rates. The active components which are part of the delivery system may be selected from sweeteners including high intensity sweeteners, acids, flavorants, pharmaceuticals, therapeutic agents, vitamins, minerals, a tooth whitener or cleaner, breath fresheners, cooling agents, warming agent, a sensate, and other materials that would benefit by coating for protection, controlled release and/or for taste masking. The active components include nicotine useful for the treatment of addiction to tobacco products and caffeine typically found in coffee and/or beverages. In one embodiment of the present invention, the active components are sweeteners, for example high intensity sweeteners such as neotame, aspartame, sucralose, acesulfame potassium and others as described herein.

It has been found in accordance with the present invention that a delivery system for delivering active components can be formulated to ensure an effective sustained release of the active components based on the type and amount of the active components and desired release profile. For example, it may be desirable to affect the release of a high intensity sweetener over a period of 25 to 30 minutes to ensure against a rapid burst of sweetness which may be offensive to some consumers. A shorter release time may be desirable for other type of active components such as pharmaceuticals or therapeutic agents, which may be incorporated into the same edible composition by using separate delivery systems for each combination of two or more active components. In accordance with the present invention, delivery systems may be formulated based on a range of release profiles relative to a standard. The standard may comprise a series of known delivery systems having, for example, a polymer encapsulating material having specific hydrophobicity and/or tensile strengths over a range. Each of the delivery systems of the standard will be associated with a particular release profile or ranges of release profiles.

In one embodiment, the present invention includes the incorporation of a plurality of delivery systems to deliver two or more active component combinations where active components may be desirably released at distinctly different release rates from the different delivery systems in order to obtain desired release profiles. The active components in each delivery system can be the same or different. Different delivery systems may use different combinations of active components and/or different encapsulating materials.

For example, high intensity sweeteners may desirably be released over an extended period of time (e.g. 20 to 30 minutes) while some pharmaceuticals are desirably released over a significantly shorter period of time.

In certain embodiments of the present invention, the delivery system can be prepared such that the release of the at least two active agents occurs within a desired release profile relative to the time of delivery. For example, in one embodiment, the delivery system can be prepared such that the release of the at least two active agents are released at a rate of 80% over the course of 15 minutes, 90% over the course of 20 minutes, and/or a 95% over the course of 30 minutes. In another embodiment, the delivery system can be prepared such that the two or more active agents are released at a rate of 25% over the course of 15 minutes, 50% over the course of 20 minutes and/or 75% over the course of 30 minutes. For example, using chewing gum as an example, the same sweetener combination can be incorporated into two different delivery systems, one of which provides an early release and second providing a more delayed release to contribute to longer lasting perceived sweetness and/or flavor by the consumer.

In one embodiment, the amount of each active component in the combination of two or more actives in a particular delivery system can be adjusted to provide a similar or substantially similar release profile of each of the two or more active during a preselected time period based on the amounts of the two or more actives added to the delivery system relative to the addition of the two or more actives in separate delivery systems or as actives free of the delivery system, e.g., non-encapsulated. In this manner, the ratio of the two or more active agents can be managed whereby the combination of actives together provides a beneficial effect upon consuming an edible composition containing the delivery system, e.g., enhanced perceived sweetness and/or flavor; and/or the action of one active can serve to minimize and/or suppress negative sensed perceptions from the other active in the delivery system, e.g., minimizing and/or suppressing perceived bitterness of one or more active. In addition, combining the two or more actives in a single delivery system enables simultaneous and/or consistent release profiles of the two or more actives when an edible composition containing the same is consumed compared to the situation where the two or more actives are in two or more separate delivery systems. Without being limited to a particular theory, one basis for this higher level of control is because each active component will generally have different hydrophobic characteristics and as a result when combined with encapsulating material, even the same type and amount thereof, the resulting delivery system has an overall different hydrophobic character and/or tensile strength. These differences will cause the different delivery systems to break down at different times and/or rates post-consumption of the edible composition containing these delivery systems. However, when combined into a single delivery system the overall characteristic of the delivery system, whether assessed by hydrophobicity and/or tensile strength, will be the same whereby the release profiles of the two active agents are more likely to be similar than when provided in separate systems.

For example, two types of active components, acesulfame potassium and aspartame have very strong qualitative and quantitative synergy. However, at ambient temperatures the solubility of these two actives are different and may result in delivery systems with different water solubilities resulting in different release rates of the two actives thereby reducing the impact of the synergy that occurs between these two sweeteners. By combining these two sweeteners into one delivery system and at a ratio based on their expected release profile, in part, due to their water solubility, one can take advantage of the synergistic action between aspartame and aceK over a longer and/or controlled period of time.

As another example, active agents such as caffeine, tooth whitening agents, and zinc (an antibacterial) often have a bitter taste when consumed (in the case of zinc, a metallic taste is perceived). However, the presence of one or more sweeteners, such as a high intensity sweetener minimizes, masks, and/or suppresses these bitter and/or metallic tastes associated with these other actives. By combining the sweetener and the caffeine, as an example, in a single delivery system, the release of both actives can be controlled such that the benefits of the sweetener can be managed better than if the actives were provided in separate delivery systems.

Hydrophobicity of the Encapsulating Material

In one aspect of the present invention, the release profile of the active components can be managed by formulating the delivery system based on the hydrophobicity of the encapsulating material, e.g., polymer. Using highly hydrophobic polymers to form a delivery system, the release of the active component can be delayed during consumption of an edible product that includes the delivery system. In a similar manner, using encapsulating material that is less hydrophobic, the active components can be released earlier or more rapidly.

Hydrophobicity can be quantitated by the relative water-absorption measured according to American Society of Testing Materials in method number ASTM D570-98. Thus, by selecting encapsulating material with relatively lower water-absorption properties and adding that to the mixer, the release of the active component contained in the produced delivery system can be delayed compared to those encapsulating materials having higher water-absorption properties. In certain embodiments, a delivery system with encapsulation material having a water absorption of from about 50 to 100% (as measured according to ASTM D570-98) can be used. To decrease the relative delivery rate of the active components or delay release of the active components, the encapsulating material can be selected such that the water absorption would be from about 15 to about 50% (as measured according to ASTM D570-98). Still further, in other embodiments, the water absorption properties of the encapsulating material can be selected to be from 0.0 to about 5% or up to about 15% (as measured according to ASTM D570-98) to create even more delay in the release of the active component.

In other embodiments, mixtures of two or more delivery systems formulated with encapsulating material having different water-absorption properties can also be used in subsequent incorporation into an edible composition. When combining two or more delivery systems, one can manage the release of the active components such that, for example, some of the active is released at an earlier stage during consumption of the edible product containing the same and some of the active is released at a later stage during consumption.

Polymers with suitable hydrophobicity which may be used in the context of the present invention include homo- and co-polymers of, for example, vinyl acetate, vinyl alcohol, ethylene, acrylic acid, methacrylate, methacrylic acid and others. Suitable hydrophobic copolymers include the following non-limiting examples, vinyl acetate/vinyl alcohol copolymer, ethylene/vinyl alcohol copolymer, ethylene/acrylic acid copolymer, ethylene/methacrylate copolymer, ethylene/methacrylic acid copolymer.

In some embodiments, the hydrophobic encapsulating material may be present in amounts of from about 0.2% to 10% by weight based on the total weight of the edible composition, including 0.3, 0.5, 0.7, 0.9, 1.0, 1.25, 1.4, 1.7, 1.9, 2.2, 2.45, 2.75, 3.0, 3.5, 4.0, 4.25, 4.8, 5.0, 5.5, 6.0, 6.5, 7.0, 7.25, 7.75, 8.0, 8.3, 8.7, 9.0, 9.25, 9.5, 9.8 and all values and ranges there between, for example, from 1% to 5% by weight. The amount of the encapsulating material will, of course, depend in part on the amount of the active components used. The amount of the encapsulating material with respect to the weight of the delivery system, is from about 30% to 99%, including 35, 40, 45, 50, 55, 60, 65, 70, 75, 80, 85, 95, 97 and all values and ranges there between, for example, from about 60% to 90% by weight.

In formulating the delivery system based on the selection criteria of hydrophobicity of the encapsulating material, the active components can be entirely encapsulated within the encapsulating material or incompletely encapsulated within the encapsulating material provided the resulting delivery system meets the criteria set forth hereinabove. The incomplete encapsulation can be accomplished by modifying and/or adjusting the manufacturing process to get partial coverage of the active components. In some embodiments, the encapsulation material may form a matrix with the active components.

For example, if ethylene-vinyl acetate is the encapsulating material, the degree of hydrophobicity can be controlled by adjusting the ratio of ethylene and vinyl acetate in the copolymer. The higher the ethylene:vinylacetate ratio, the slower the release of the active component. Using vinylacetate/ethylene copolymer as an example, the ratio of the vinylacetate/ethylene in the copolymer can be from about 1 to about 60%, including ratios of 2.5, 5, 7.5, 9, 12, 18, 23, 25, 28, 30, 35, 42, 47, 52, 55, 58.5% and all values and ranges there between.

One embodiment of the present invention is a method of selecting a target delivery system containing two or more active components for an edible composition based on the hydrophobicity of the encapsulating material. The method generally includes preparing a targeted delivery system containing active components, an encapsulating material and optional additives, with the encapsulating material having a pre-selected hydrophobicity. The hydrophobicity of the encapsulating material employed in the targeted delivery system is pre-selected to provide a desirable release profile of the active components. This selection of the encapsulating material is based on the hydrophobicity of sample delivery systems having the same or similar active components and known release profiles of the active components.

In another embodiment of the invention, the method comprises (a) obtaining a plurality of sample delivery systems comprising two or more active component, at least one encapsulating material, and optional additives, wherein each of the delivery systems is prepared with different encapsulating materials having different hydrophobicities; (b) testing the sample delivery systems to determine the respective release profiles of the active components; and (c) formulating a target delivery system containing the same active components with a hydrophobic encapsulating material corresponding to a desired release profile of the active components based on the obtained sample delivery systems.

The method of selecting at least one delivery system suitable for incorporation into an edible composition can begin by determining a desired release profile for two or more active components (i.e. a first active combination). The determination of the desired release rate may be from known literature or technical references or by in vitro or in vivo testing. Once the desired release profile is determined, the desired hydrophobicity of the encapsulating material can be determined (i.e. a first hydrophobic encapsulating material) for a delivery system (i.e. first delivery system) that can release the first active combination at the desired release. Once the delivery system is obtained which can deliver the active components as required it is then selected for eventual inclusion in an edible composition.

The method described above may then be repeated for a second active combination and for additional active components as described via the determination and selection of a suitable delivery system.

The edible compositions may contain two or more types of delivery systems, each containing the same or different combinations of active components, the selection of delivery systems based on the hydrophobicity of the encapsulating material and/or the tensile strength of the delivery systems as described in the following. Additionally or alternatively, one or more delivery systems may be incorporated into an edible composition with free (non-encapsulated) active components, such as aspartame, sucralose, neotame and ace K sweeteners.

Tensile Strength of the Delivery System

In a further embodiment, the selection of a delivery system, in addition to or independently from being based on the hydrophobic character of the encapsulating material, can be selected based on the manipulation and selection of the tensile strength of the encapsulating material to provide a delayed and/or controlled release of the active component. Thus, the controlled and/or delayed release of the active component can be controlled by selecting a predetermined tensile strength and/or a predetermined hydrophobicity of the encapsulating material.

As used herein, the term "tensile strength" means the maximum stress a material subjected to a stretching load can withstand without tearing. A standard method for measuring tensile strength of a given substance is defined by the American Society of Testing Materials in method number ASTM-D638.

The predetermined tensile strength is determined based, in part, on the active components and the desired release time of the same. The predetermined tensile strength may be selected from a standard comprised of one or more delivery systems with each standard delivery system having a known release rate of the desired active component or combination of components. The delivery system of the present invention may further provides the active components with a protective barrier against moisture and other conditions such as pH changes, reactive compounds and the like, the presence of which can undesirably degrade the active components.

It will be understood that a plurality of delivery systems may be prepared in this manner each containing a different active component by utilizing a comparison with standard delivery systems containing such different active components.

By maintaining the tensile strength of the delivery system within a preselected desirable range, the two or more active components are released from the composition in a highly controlled and consistent manner. By focusing on the tensile strength of the delivery system, the process for selecting and formulating suitable delivery systems is enhanced in a manner which effectively reduces the need for trial and error experimentation typically necessary in prior art systems.

The desired tensile strength of the delivery system can be readily determined within a desired range. In one embodiment of the present invention, the tensile strength of the delivery system is at least 6,500 psi, including 7500, 10,000, 20,000, 30,000, 40,000, 50,000, 60,000, 70,000, 80,000, 90,000, 100,000, 125,000, 135,000, 150,000, 165,000, 175,000, 180,000, 195,000, 200,000 and all ranges and subranges there between, for example a tensile strength range of 6,500 to 200,000 psi. The formulation of a delivery system with a desirable tensile strength can be made from a variety of encapsulating materials and at least one additive which hereinafter are referred to as "at least one tensile strength modifying agent or modifier." The at least one additive may be used to formulate the delivery system by modifying the tensile strength of the delivery system, including tensile strength-lowering materials such as fats, emulsifiers, plasticizers (softeners), waxes, low molecular weight polymers, and the like, in addition to tensile strength increasing materials such as high molecular weight polymers. In addition, the tensile strength of the delivery system can also be fine tuned by combining different tensile strength modifiers to form the delivery system. For example, the tensile strength of high molecular weight polymers such as polyvinyl acetate may be reduced when tensile strength lowering agents such as fats and/or oils are added.

In one embodiment of the present invention, at least one tensile strength modifying agent is present in the delivery system in an amount sufficient such that the release of the active agents contained in the delivery system is released at a rate of 80% over the course of 15 minutes, 90% over the course of 20 minutes, and/or 95% over the course of 30 minutes. In another embodiment, the at least one tensile strength modifying agent is present in the delivery system in an amount sufficient such that the active agents are released at a rate of 25% over the course of 15 minutes, 50% over the course of 20 minutes and/or 75% over the course of 30 minutes.

In another embodiment of the present invention, the at least one tensile strength modifying agent is present in the delivery system in an amount sufficient such that the tensile strength of the delivery system is at least about 6,500 psi, including 7500, 10,000, 20,000, 30,000, 40,000, 50,000, 60,000, 70,000, 80,000, 90,000, 100,000, 125,000, 135,000, 150,000, 165,000, 175,000, 180,000, 195,000, 200,000 and all ranges and subranges there between, for example a tensile strength range of 6,500 to 200,000 psi.

Examples of tensile strength modifiers or modifying agents include, but are not limited to, fats (e.g., hydrogenated or non-hydrogenated vegetable oils, animal fats), waxes (e.g., microcrystalline wax, bees wax), plasticizers/emulsifiers (e.g., mineral oil, fatty acids, mono- and diglycerides, triacetin, glycerin, acetylated monoglycerides, glycerol rosin monostearate esters), low and high molecular weight polymers (e.g., polypropylene glycol, polyethylene glycol, polyisobutylene, polyethylene, polyvinylacetate) and the like, fillers like talc, dicalcium phosphate, silica, calcium carbonate, and combinations thereof. Plasticizers may also be referred to as softeners.

Thus, by employing tensile strength modifiers, the overall tensile strength of the delivery system can be adjusted or altered in such a way that a preselected tensile strength is obtained for the corresponding desired release profile of the active components from an edible composition based on a comparison with a standard.

The delivery systems of the present invention produce controlled release of the active components as desired through the use of a preselected tensile strength when matched with a desirable release profile selected according to the type of the active components used, the encapsulating material used, the additives incorporated, the desired rate of release of the active component, and the like. The encapsulating materials used for the delivery system are generally selected from edible water insoluble materials capable of forming a strong matrix, solid coating or film as a protective barrier around the active component. The encapsulating material is chosen in a manner consistent with the tensile strength of the delivery system which can be at least 6,500 psi, including 7500, 10,000, 20,000, 30,000, 40,000, 50,000, 60,000, 70,000, 80,000, 90,000, 100,000, 125,000, 135,000, 150,000, 165,000, 175,000, 180,000, 195,000, 200,000 and all ranges and subranges there between, for example a tensile strength range of 6,500 to 200,000 psi. Such encapsulating materials may be selected from polyvinyl acetate, polyethylene, crosslinked polyvinyl pyrrolidone, polymethylmethacrylate, polylactic acid, polyhydroxyalkanoates, ethylcellulose, polyvinyl acetatephthalate, polyethylene glycol esters, methacrylicacid-co-methylmethacrylate, and the like, and combinations thereof.

The encapsulating material, based on the selection of hydrophobicity of the encapsulating material and/or the tensile strength of the delivery system, may be present in amounts of from about 0.2% to 30% by weight based on the total weight of the edible composition, including 0.3, 0.5, 0.7, 0.9, 1.0, 1.25, 1.4, 1.7, 1.9, 2.2, 2.45, 2.75, 3.0, 3.5, 4.0, 4.25, 4.8, 5.0, 5.5, 6.0, 6.5, 7.0, 7.25, 7.75, 8.0, 8.3, 8.7, 9.0, 9.25, 9.5, 9.8, 12, 14, 15, 18, 21, 24, 26, 28 and all values and ranges there between, for example, from 1% to 5% by weight. The amount of the encapsulating material will, of course, depend in part on the amount of the active component present in the delivery system. The amount of the encapsulating material with respect to the weight of the delivery system, is from about 30% to 99%, including 35, 40, 45, 50, 55, 60, 65, 70, 75, 80, 85, 95, 97 and all values and ranges there between, for example, from about 60% to 90% by weight.

The tensile strength of the delivery system may be selected from relatively high tensile strengths when a relatively slower or delay release is desired and relatively lower tensile strengths when a faster or quicker release is desired. Thus, when employing a tensile strength of 50,000 for a delivery system, the release of the active component, will generally be delayed in comparison to the release of the active components in a delivery system having a tensile strength of 10,000 psi regardless of the type of encapsulating material (e.g. polyvinyl acetate) chosen as long as the hydrophobicity of the encapsulations is kept consistently similar or identical.

In one embodiment of the present invention, the encapsulating material is polyvinyl acetate. A representative example of a polyvinyl acetate product suitable for use as an encapsulating material in the present invention is Vinnapas® B100 sold by Wacker Polymer Systems of Adrian, Mich. A delivery system utilizing polyvinyl acetate may be prepared by melting a sufficient amount of polyvinyl acetate at a temperature of about 65° to 120° C. for a short period of time, e.g., 5 minutes. The melt temperature will depend on the type and tensile strength of the polyvinyl acetate encapsulating material where higher tensile strength materials will generally melt at higher temperatures. Once the encapsulating material is melted, a suitable amount of the active components (e.g., high intensity sweeteners such as aspartame and aceK) are added and blended into the molten mass thoroughly for an additional short period of mixing. The resulting mixture is a semi-solid mass, which is then cooled (e.g., at 0° C.) to obtain a solid, and then ground to a U.S. Standard sieve size of from about 30 to 200 (900 to 75 microns). The tensile strength of the resulting delivery system can readily be tested according to ASTM-D638 after molding the encapsulations in required size and shape.

The selection of a suitable encapsulating material will also depend in part on the type and amount of the active components and the presence of other additives or ingredients. Plasticizers or softeners as well as fats and oils, for example, act as "tensile strength modifying agents" and may be incorporated into the delivery system and particularly into the encapsulating material to modify the tensile strength of the resulting delivery system. The above mentioned additives may be added to the encapsulating material during the molten state. The amount of additives used in the delivery system of the present invention will of course vary according to the desired tensile strength can range up to 40% by weight based on the total weight of the delivery system.

In formulating the delivery system to have a predetermined tensile strength and/or a preselected hydrophobic encapsulating material, the active components can be entirely encapsulated within the encapsulating material or incompletely encapsulated within the encapsulating material provided the resulting tensile strength of the delivery system meets the criteria set forth hereinabove. The incomplete encapsulation can be accomplished by modifying and/or adjusting the manufacturing process to get partial coverage of the active components.

The presence of fats and oils as an additive has been found to have two effects on the delivery system. The first effect is observed at lower concentrations, i.e. up to 5% by weight, including up to 4.7, up to 4.5, up to 4.25, up to 4.0, up to 3.5, up to 3.0, up to 2.5, up to 2.25, up to 2.0, up to 1.75, up to 1.5, up to 1.0 and all values and ranges therebetween, wherein the fats and/or oils either maintain or increase the tensile strength of the delivery system. At higher concentrations (i.e., typically above 5% by weight), the fats and/or oils tend to reduce the tensile strength of the delivery system. Even with such unusual or non-linear effects on the tensile strength of the delivery system, a suitable delivery system with the desired release of the active component may be readily formulated in accordance with the present invention because the targeted delivery system is prepared based on sample delivery systems having known release profiles for the active component.

In a one embodiment of the present invention, there is provided a method of selecting a target delivery system containing two or more active components for an edible composition based on the hydrophobicity of the encapsulating material and/or the tensile strength of the delivery system. The method generally includes preparing a targeted delivery system containing an active component, an encapsulating material and optional additives, with the encapsulating material having a pre-selected hydrophobicity and the targeted delivery system having a pre-selected tensile strength. The tensile strength of the targeted delivery system and/or the hydrophobicity of the encapsulating material is pre-selected to provide a desirable release profile of the active component. This selection of the tensile strength is based on the tensile strengths of sample delivery systems having the same or similar active component and known release profiles of the active component. Likewise, the selection of the encapsulating material is based on the hydrophobicity of sample delivery systems having the same or similar active component and known release profiles of the active component.

In a another embodiment of the invention, the method comprises the steps of (a) obtaining a plurality of sample delivery systems comprising two or more active components, at least one encapsulating material, and optional additives, wherein each of the delivery systems has a different tensile strength and encapsulating material having a different hydrophobicity; (b) testing the sample delivery systems to determine the respective release profiles of the active components; and (c) formulating a target delivery system containing the same active components with a tensile strength and hydrophobicity of the encapsulating material corresponding to a desired release profile of the active components based on the obtained sample delivery systems.

The method of selecting at least one delivery system suitable for incorporation into an edible composition can begin by determining a desired release profile for an active component (i.e. a first active component). The determination of the desired release profile may be from known literature or technical references or by in vitro or in vivo testing. Once the desired release profile is determined, it is typical to determine the desired tensile strength and the desired hydrophobicity of the encapsulating material for a delivery system that can release the first active component at the desired release. Once the delivery system is obtained which can deliver the active components as required it is then selected for eventual inclusion in an edible composition.

The method described above may then be repeated for a second active component and for additional active components as described via the determination and selection of a suitable delivery system.

One of the desirable properties of solid dosage forms, such as an edible composition or a chewing gum, is that release of the active component, such as a sweetener, can be uniform throughout the chew time. For example, with free (non-encapsulated) sweeteners, the release rate is quick and the taste of gum is not desirable at the late chewing time. With delivery systems having a high tensile strength, the release rate is delayed so that the sweetener releases late in chewing time. To balance early and late release rates of the active components, for example, an edible composition can be manufactured so that it contains a mixture of free actives with delivery systems having high tensile strength and/or hydrophobicity and/or combinations of two or more delivery systems having different tensile strength and/or hydrophobicities designed such that the active component is released at different rates.

In some instances, some of the active components in the delivery system may be miscible with the encapsulating material. For example, polyvinylacetate is one type of encapsulating material that can be used in the present invention. Some components, such as flavor which are short or medium chain esters, may interact with the polyvinylacetate (PVAc) and thereby reduce the effectiveness of the controlled and/or delayed release profile of the active component.

Therefore, one embodiment of the present invention, by itself or combined with the other embodiments described herein, is coating at least one of the active components with a "coating material" that is not miscible or at least less miscible relative to its miscibility with the encapsulating material. The active component can be coated with the coating material prior to or concurrently with its encapsulation with the encapsulating material. Both active components or if more than two, all of the actives, ma also be coated in a similar manner, each active being coated with the same or different coating materials.

The coating material according to the present invention can reduce the miscibility of the active component with the encapsulating material at least 5%, preferably 25%, more preferably at least 50%, including, 10, 15, 20, 30, 40, 60, 70, 75, 80, 85, 90, 95% or more relative to the miscibility of the active component which is not coated by the coating material.

In one embodiment, the material used to coat the active component is a water soluble and/or hydrophilic material. Non-limiting examples of suitable coating materials include, gum Arabic, cellulose, modified cellulose, gelatin, polyols (eg., sorbitol, maltitol), cyclodextrin, zein, polyvinyl alcohol, polymethylmethacrylate, and polyurethane. Mixtures of various coating materials may also be used.

The coating thickness will vary depending on starting particle size and shape of the active material as well as the desired weight percent coating level. In accordance with the present invention, the coating thickness is preferably from about 1 to about 200 microns, including 10, 20, 30, 40, 50, 60, 70, 80, 90, 100, 110, 120, 130, 140, 150, 160, 170, 180 and 190 microns and all values and ranges there between, for example, the thickness of coating material can be from about 10 to about 50 microns and 20 to 54% by weight.

In addition to providing a barrier stability that can reduce and/or eliminate the miscibility of the active component, the coating material used in the present invention may also have good film forming properties which facilitates the formation of a barrier between the active component and the encapsulating material. Film forming properties as used herein means that the coating material, after dissolution in at least one solvent (such as, for example, water and/or organic solvents), leaves a film on the active component to which it is applied, for example, once the at least one solvent evaporates, absorbs and/or dissipates on the active component. Furthermore, when the coating material is used in the preparation of edible compositions, such as chewing gum, one of ordinary skill in the art recognizes that the coating material should be chosen based on its taste, shelf life, stickiness, resistance to microbial growth, and other common criteria for selecting ingredients for consumption.

The active component can be coated with the coating material by applying the coating material to the active component using a pan, spray, batch, and/or continuous processes typically used to coat materials. In one embodiment, the coating material is dissolved or dispersed in a solvent to facilitate coating on the active component. The coating material can be delivered using conventional methods of coating substrates. In a preferred method of coating, a fluidized bed technique is employed which is described, for example, in U.S. Pat. No. 3,196,827, the relevant contents of which are incorporated herein by reference.

In a further embodiment, by coating the active component and encapsulating the active component according to the description provided herein, a longer shelf life of the edible compositions can be attained. As used herein, shelf life is an indicia of the stability of the components of the edible compositions containing the active component. Using flavorants and/or sweeteners for illustration, this increase in shelf life can be assessed by determining the perceived flavor and/or sweetness of the flavorant and/or sweetener contained in the composition. According to the present invention, when using a coating material to coat the active component a 5% increase in shelf life relative to a similar product in which the active component has not been coated with the barrier material can be achieved, including 10, 20, 30, 40, 50, 60, 70, 80, 90, 100% or more, as well as all values and ranges there between, increased shelf life. In another embodiment, the longer shelf life can be correlated to the time of storage after manufacture, for example at 10 weeks the shelf life the composition containing the coated active component will demonstrate a 50%, 75%, 80%, or 90% improvement relative to a similar composition but not containing an active component coated with a coating material according to the invention described herein. In a further example, at 24 weeks of storage, the coated active component will show an 80 to 90% improvement relative to a similar composition but not containing the active component coated with a coating material as according to the invention described herein.

In another embodiment of the present invention, the active components can encapsulated into the delivery system used to provide controlled and/or delayed release by forming a polymer matrix. In the formation of a polymer matrix, the encapsulating material is mixed with the active components in an amount sufficient to encapsulate the active components and thereafter compressed into a tablet at or about ambient temperature. Heating up to but not exceeding the softening point of the encapsulating material further form the compressed tablet. The formation of the tablet with compression and under relatively low heat facilitates the encapsulation of active ingredients that are susceptible to heat degradation or relatively unstable when heat is applied.

A compression force from about 7 to about 28 KN (about 1573-6300 lbf) can be used, including 6, 8, 10, 12, 14, 15, 16, 18, 20, 22, 24, 26, 27, 28.5 and all values and subranges there between. In one embodiment, the polymer matrix encapsulating the active component can be made using a Piccola Model D-8 laboratory rotary tablet press.

In certain embodiments, the polymer matrix formed at or about ambient temperature can be mixed with other polymer matrices formed in the same way and/or the other delivery systems described herein. By combining various delivery systems, a profile of release of different or the same ingredients can be controlled, e.g., to have fast release from one and a longer, delayed release from a second.

The polymer encapsulating material used for the preparation of the polymer matrix can be chosen such that it has sufficient tensile strength, sufficient adhesion properties, be chemically inert, and/or sufficient hydrophobicity to permit suitable controlled release of the encapsulated active component. Non-limiting examples of polymers which can be used to form the polymer matrix include polyvinyl acetate, polyethylene, cross-linked polyvinyl pyrrolidone, polymethylmethacrylate, polylactidacid, polyhydroxyalkanoates, ethylcellulose, polyvinyl acetatephthalate, polyethylene glycol esters, methacrylicacid-co-methylmethacrylate, and the like. Combinations of polymers may also be used.

The polymer encapsulating material may be present in amounts of from about 0.2% to 10% by weight based on the total weight of the edible composition, including 0.3, 0.5, 0.7, 0.9, 1.0, 1.25, 1.4, 1.7, 1.9, 2.2, 2.45, 2.75, 3.0, 3.5, 4.0, 4.25, 4.8, 5.0, 5.5, 6.0, 6.5, 7.0, 7.25, 7.75, 8.0, 8.3, 8.7, 9.0, 9.25, 9.5, 9.8 and all values and ranges there between, for example, from 1% to 5% by weight. The amount of the encapsulating material will, of course, depend in part on the amount of the active component which must be encapsulated. The amount of the encapsulating material with respect to the weight of the delivery system, is from about 30% to 99%, including 35, 40, 45, 50, 55, 60, 65, 70, 75, 80, 85, 95, 97 and all values and ranges there between, for example, from about 60% to 90% by weight.

The active component can be entirely encapsulated with the encapsulating material constituting the polymer matrix or incompletely encapsulated within the encapsulating material provided the delivery system meets the preselected criteria for extended and/or delayed release of the active component. The incomplete encapsulation can be accomplished by modifying and/or adjusting the manufacturing process to get partial coverage of the active component.

The polymer matrix used as a delivery system for active components in a similar manner as those described hereinabove. Like those delivery systems the polymer matrix can be prepared to a desired tensile strength and/or the selection of encapsulating material based on its hydrophobicity to permit the delivery of the active component at a controlled and/or delayed release profile having the desired characteristics as described hereinabove. As described hereinabove, the tensile strength of the polymer matrix can be modified using tensile strength modifiers or modifying agents as described hereinabove.

In a preferred embodiment, the tensile strength of the polymer matrix ranges from about 4000 to about 300,000 psi after the heating step, including 5000, 10000, 25000, 50,000, 75000, 90,000, 100000, 125000, 155000, 180000, 205000, 230000, 255000, 270000, 295000 psi and all values and subranges there between.

In a one embodiment of the present invention, there is provided a method of selecting a target delivery system constituting a polymer matrix containing an active component for an edible composition based on the hydrophobicity of the encapsulating material and/or the tensile strength of the delivery system. The method generally includes preparing a polymer matrix containing an active component, an encapsulating material and optional additives, with the encapsulating material having a pre-selected hydrophobicity and/or a pre-selected tensile strength. The tensile strength of the polymer matrix and/or the hydrophobicity of the encapsulating material is pre-selected to provide a desirable release profile of the active component. This selection of the tensile strength is based on the tensile strengths of sample polymer matrices having the same or similar active component and known release profiles of the active component. Likewise, the selection of the encapsulating material is based on the hydrophobicity of sample polymer matrices having the same or similar active component and known release rates of the active component.

In another embodiment of the invention, the method comprises the steps of (a) obtaining a plurality of sample polymer matrices comprising an active component, at least one encapsulating material, and optional additives, wherein each of the polymer matrices has a different tensile strength and/or encapsulating material having a different hydrophobicity; (b) testing the sample polymer matrices to determine the respective release profiles of the active component; and (c) formulating a target polymer matrix containing the same active component with a tensile strength and/or hydrophobicity of the encapsulating material corresponding to a desired release profile of the active component based on the obtained sample polymer matrices.

The method of selecting at least one polymer matrix suitable for incorporation into an edible composition can begin by determining a desired release profile for an active component (i.e. a first active component). The determination of the desired release profile may be from known literature or technical references or by in vitro or in vivo testing. Once the desired release profile is determined, it is typical to determine the desired tensile strength and/or the desired hydrophobicity of the encapsulating material used for the polymer matrix that can release the first active component at the desired release. Once the polymer matrix is obtained which can deliver the active component as required it is then selected for eventual inclusion in an edible composition.

The method described above may then be repeated for a second active component and for additional active components as described via the determination and selection of a suitable polymer matrix.

In some embodiments, the delivery system may be in the form of a powder or granules. The particle size, generally, can vary and not have a significant effect on the function of the present invention. In one embodiment, the average particle size is desirably selected according to the desired rate of release and/or mouthfeel (i.e., grittiness) and the type of carrier incorporated in the edible composition. Thus, in certain embodiments of the present invention, the average particle size is from about 75 to about 600 microns, including 100, 110, 140, 170, 200, 230, 260, 290, 320, 350, 370 and all values and ranges there between. As the values are an average, one will appreciate within a given sample of powder or granules, there may be particles with sizes greater and/or less than the numerical values provided. In one embodiment of the invention, where the delivery system is incorporated into a chewing gum, the particle size can be less than 600 microns.

The active components incorporated into the delivery system manufactured according to the processes described herein include, for example, a sweetener, such as a high-intensity sweetener, an acid, e.g., a food grade acid, a flavorant, a pharmaceutical, a therapeutic agent, a vitamin, a mineral, a breath freshener, a tooth whitener or cleaner, a cooling agent, a warming agent, a sensate, throat-soothing agents, spices, caffeine, drugs, etc. Combinations of these active components can be included in the same or different delivery systems. Such components may be used in amounts sufficient to achieve their intended effects.

A variety of well known cooling agents may be employed. For example, among the useful cooling agents are included menthol, xylitol, menthane, menthone, ketals, menthone ketals, menthone glycerol ketals, substituted p-menthanes, acyclic carboxamides, substituted cyclohexanamides, substituted cyclohaxane carboxamides, substituted ureas and sulfonamides, substituted menthanols, hydroxymethyl and hydroxymethyl derivatives of p-menthane, 2-mercapto-cyclo-decanone, 2-isopropanyl-5-methylcyclohexanol, hydroxycarboxylic acids with 2-6 carbon atoms, cyclohexanamides, menthyl acetate, menthyl lactate, menthyl salicylate, N,N 2,3-trimethyl-2-isopropyl butanamide (WS-23), N-ethyl-p-menthane-3-carboxamide (WS-3), menthyl succinate, 3,1-menthoxypropane 1,2-diol, among others. These and other suitable cooling agents are further described in the following U.S. patents, all of which are incorporated in their entirety by reference hereto: U.S. Pat. Nos. 4,230,688; 4,032,661; 4,459,425; 4,136,163; 5,266,592; 6,627,233.

Examples of food grade acids which can be used include acetic acid, adipic acid, ascorbic acid, butyric acid, citric acid, formic acid, fumaric acid, glyconic acid, lactic acid, phosphoric acid, malic acid, oxalic acid, succinic acid, tartaric acid and others. Combinations of food grade acids may also be used.

Warming components may be selected from a wide variety of compounds known to provide the sensory signal of warming to the user. These compounds offer the perceived sensation of warmth, particularly in the oral cavity, and often enhance the perception of flavors, sweeteners and other organoleptic components. Among the useful warming compounds included are vanillyl alcohol n-butylether (TK-1000) supplied by Takasago Perfumary Company Limited, Tokyo, Japan, vanillyl alcohol n-propylether, vanillyl alcohol isopropylether, vanillyl alcohol isobutylether, vanillyl alcohol n-aminoether, vanillyl alcohol isoamylether, vanillyl alcohol n-hexylether, vanillyl alcohol methylether, vanillyl alcohol ethylether, gingerol, shogaol, paradol, zingerone, capsaicin, dihydrocapsaicin, nordihydrocapsaicin, homocapsaicin, homodihydrocapsaicin, ethanol, isopropyl alcohol, iso-amylalcohol, benzyl alcohol, glycerine, and combinations thereof.

The sensation of warming or cooling effects may be prolonged with the use of a hydrophobic sweetener as described in U.S. Patent Application Publication 2003/0072842 A1 which is incorporated in its entirety herein by reference. For example, such hydrophobic sweeteners include those of the formulae I-XI referenced therein. Perillartine may also be added as described in U.S. Pat. No. 6,159,509 also incorporated in its entirety herein by reference.

The breath freshening agents may include in addition to the flavors and cooling agents described hereinabove, a variety of compositions with odor controlling properties. These may include, without limitation, cyclodextrin and magnolia bark extract. The breath freshening agents may further be encapsulated to provide a prolonged breath freshening effect. Examples of malodor-controlling compositions are included in U.S. Pat. No. 5,300,305 to Stapler et al. and in U.S. Patent Application Publication Nos. 2003/0215417 and 2004/0081713 which are incorporated in their entirety herein by reference.

As described above, a variety of oral care products may also be included in some embodiments of chewing gums. These may include tooth whiteners, stain removers and anti-calculus agents. Examples of these include, but are not limited to hydrolytic agents including proteolytic enzymes, abrasives such as hydrated silica, calcium carbonate, sodium bicarbonate and alumina, other active stain-removing components such as surface-active agents, such as anionic surfactants such as sodium stearate, sodium palminate, sulfated butyl oleate, sodium oleate, salts of fumaric acid, glycerol, hydroxylated lecithin, sodium lauryl sulfate and chelators such as polyphosphates, which are typically employed in dentifrice compositions as tartar control ingredients. Also included are tetrasodium pyrophosphate and sodium tripolyphosphate, xylitol, hexametaphosphate, and an abrasive silica. Further examples are included in the following U.S. Patents which are incorporated in their entirety herein by reference: U.S. Pat. Nos. 5,227,154, 5,378,131 and 6,685,916.

A variety of drugs, including medications, herbs, and nutritional supplements may also be included in the gum formulations. Examples of useful drugs include ACE-inhibitors, antianginal drugs, anti-arrhythmias, anti-asthmatics, anticholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies such as sildenafil citrate, which is currently marketed as Viagra®, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocins, parasympatholytics, parasympathomimetics, prostaglandins, psychotherapeutic agents, respiratory agents, sedatives, smoking cessation aids such as bromocryptine or nicotine, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

Examples of other active ingredients include antacids, H2-antagonists, and analgesics. For example, antacid dosages can be prepared using the ingredients calcium carbonate alone or in combination with magnesium hydroxide, and/or aluminum hydroxide. Moreover, antacids can be used in combination with H2-antagonists. Active antacid ingredients include, but are not limited to, aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

Analgesics include opiates and opiate derivatives, such as OXYCONTIN®, ibuprofen, aspirin, acetaminophen, and combinations thereof that may optionally include caffeine.

Other drug ingredients for use in embodiments include anti-diarrheals such as immodium AD, anti-histamines, anti-tussives, decongestants, vitamins, and breath fresheners. Also contemplated for use herein are anxiolytics such as XANAX®; anti-psychotics such as clozaril and Haldol; non-steroidal anti-inflammatories (NSAID's) such as ibuprofen, naproxen sodium, VOLTAREN® and LODINE®, anti-histamines such as CLARITIN®, HISMANAL®, RELAFEN®, and TAVIST®; anti-emetics such as KYTRIL®1 and CESAMET®; bronchodilators such as BENTOLIN®, PROVENTIL®; anti-depressants such as PROZAC®, ZOLOFT®, and PAXIL®; anti-migraines such as IMIGRA®, ACE-inhibitors such as Vasotec, Capoten and Zestril; anti-Alzheimer's agents, such as Nicergoline; and CaH-antagonists such as PROCARDIA®, ADALAT®, and Calan.

H2-antagonists which can be used include cimetidine, ranitidine hydrochloride, famotidine, nizatidien, ebrotidine, mifentidine, roxatidine, pisatidine and aceroxatidine A variety of other nutritional supplements may also be included, such as vitamin or mineral as mentioned above. For example, vitamin A, vitamin C, vitamin D, vitamin E, vitamin K, vitamin B6, vitamin B12, thiamine, riboflavin, biotin, folic acid, niacin, pantothenic acid, sodium, potassium, calcium, magnesium, phosphorus, sulfur, chlorine, iron, copper, iodine, zinc, selenium, manganese, choline, chromium, molybdenum, fluorine, cobalt and combinations thereof, may be used.

Examples of nutritional supplements are set forth in U.S. Patent Application Publication Nos. 2003/0157213 A1, 2003/0206993 and 2003/0099741 A1 which are incorporated in their entirety herein by reference.

Various herbs may also be included such as those with various medicinal or dietary supplement properties. Herbs are generally aromatic plants or plant parts that can be used medicinally or for flavoring. Suitable herbs can be used singly or in various mixtures. Examples include Echinacea, Goldenseal, Calendula, Aloe, Blood Root, Grapefruit Seed Extract, Black Cohosh, Cranberry, Ginko Biloba, St. John's Wort, Evening Primrose Oil, Yohimbe Bark, Green Tea, Maca, Bilberry, Lutein, and combinations thereof.

Flavorants which may be used include those flavors known to the skilled artisan, such as natural and artificial flavors.

These flavorings may be chosen from synthetic flavor oils and flavoring aromatics and/or oils, oleoresins and extracts derived from plants, leaves, flowers, fruits, and so forth, and combinations thereof. Nonlimiting representative flavor oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Also useful flavorings are artificial, natural and synthetic fruit flavors such as vanilla, and citrus oils including lemon, orange, lime, grapefruit, and fruit essences including apple, pear, peach, grape, blueberry, strawberry, raspberry, cherry, plum, pineapple, apricot and so forth. These flavoring agents may be used in liquid or solid form and may be used individually or in admixture. Commonly used flavors include mints such as peppermint, menthol, spearmint, artificial vanilla, cinnamon derivatives, and various fruit flavors, whether employed individually or in admixture. Flavors may also provide breath freshening properties, particularly the mint flavors when used in combination with the cooling agents, described herein below.

Other useful flavorings include aldehydes and esters such as cinnamyl acetate, cinnamaldehyde, citral diethylacetal, dihydrocarvyl acetate, eugenyl formate, p-methylamisol, and so forth may be used. Generally any flavoring or food additive such as those described in Chemicals Used in Food Processing, publication 1274, pages 63-258, by the National Academy of Sciences, may be used. This publication is incorporated herein by reference. This may include natural as well as synthetic flavors.

Further examples of aldehyde flavorings include but are not limited to acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavors), butyraldehyde (butter, cheese), valeraldehyde (butter, cheese), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, i.e., melonal (melon), 2,6-dimethyloctanal (green fruit), and 2-dodecenal (citrus, mandarin), cherry, grape, blueberry, blackberry, strawberry shortcake, and mixtures thereof.

The sweeteners used may be selected from a wide range of materials including water-soluble sweeteners, water-soluble artificial sweeteners, water-soluble sweeteners derived from naturally occurring water-soluble sweeteners, dipeptide based sweeteners, and protein based sweeteners, including mixtures thereof. Without being limited to particular sweeteners, representative categories and examples include:

(a) water-soluble sweetening agents such as dihydrochalcones, monellin, steviosides, glycyrrhizin, dihydroflavenol, and sugar alcohols such as sorbitol, mannitol, maltitol, and L-aminodicarboxylic acid aminoalkenoic acid ester amides, such as those disclosed in U.S. Pat. No. 4,619,834, which disclosure is incorporated herein by reference, and mixtures thereof;

(b) water-soluble artificial sweeteners such as soluble saccharin salts, i.e., sodium or calcium saccharin salts, cyclamate salts, acesulfame salts, such as the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and mixtures thereof;

(c) dipeptide based sweeteners, such as L-aspartic acid derived sweeteners, such as L-aspartyl-L-phenylalanine methyl ester (Aspartame) and materials described in U.S. Pat. No. 3,492,131, L-alphaaspartyl-N-(2,2,4,4-tetramethyl-3-thietanyl)-D-alaninamide hydrate (Alitame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(1-cyclohexen)-alanine, neotame, and mixtures thereof;

(d) water-soluble sweeteners derived from naturally occurring water-soluble sweeteners, such as stevosides, chlorinated derivatives of ordinary sugar (sucrose), e.g., chlorodeoxysugar derivatives such as derivatives of chlorodeoxysucrose or chlorodeoxygalactosucrose, known, for example, under the product designation of Sucralose; examples of chlorodeoxysucrose and chlorodeoxygalactosucrose derivatives include but are not limited to: 1-chloro-1'-deoxysucrose; 4-chloro-4-deoxy-alpha-D-galactopyranosyl-alpha-D-fructofuranoside, or 4-chloro-4-deoxygalactosucrose; 4-chloro-4-deoxy-alpha-D-galactopyranosyl-1-chloro-1-deoxy-beta-D-fructofuranoside, or 4,1'-dichloro-4,1'-dideoxygalactosucrose; 1',6'-dichloro 1',6'-dideoxysucrose; 4-chloro-4-deoxy-alpha-D-galactopyranosyl-1,6-dichloro-1,6-dideoxy-beta-D-fructofuranoside, or 4,1',6'-trichloro-4,1',6'-trideoxygalactosucrose; 4,6-dichloro-4,6-dideoxy-alpha-D-galactopyranosyl-6-chloro-6-deoxy-beta-D-fructofuranoside, or 4,6,6'-trichloro-4,6,6'-trideoxygalactosucrose; 6,1',6'-trichloro-6,1',6'-trideoxysucrose; 4,6-dichloro-4,6-dideoxy-alpha-D-galactopyranosyl-1,6-dichloro-1,6-dideoxy-beta-D-fructofuranoside, or
4,6,1',6'-tetrachloro 4,6,1',6'-tetradeoxygalacto-sucrose; and 4,6,1',6'-tetradeoxy-sucrose, and mixtures thereof;

(e) protein based sweeteners such as thaumaoccous danielli (Thaumatin I and II), talin, and (f) amino acid based sweeteners.

The intense sweetening agents may be used in many distinct physical forms well-known in the art to provide an initial burst of sweetness and/or a prolonged sensation of sweetness. Without being limited thereto, such physical forms include free forms, such as spray dried, powdered, beaded forms, encapsulated forms, and mixtures thereof. In one embodiment, the sweetener is a high intensity sweetener such as aspartame, sucralose, and acesulfame potassium (Ace-K).

The active component (e.g., sweetener), which is part of the delivery system, may be used in amounts necessary to impart the desired effect associated with use of the active component (e.g., sweetness). With respect to their presence in the delivery system, the active components may be present in amounts of from about 1% to 70% by weight based on the total weight of the delivery system, including 5, 10, 15, 20, 25, 30, 35, 40, 45, 50, 55, 60, 65% by weight, and all values and ranges there between, for example, from about 10% to 40% by weight based on the total weight of the delivery system. For typical edible compositions including chewing gum compositions, confectionery compositions and beverage compositions, the sweeteners may be present in amounts of from about 0.1% to 6% by weight based on the total weight of the edible composition, including 0.5, 1, 2, 3, 4, 5% by weight and all values and subranges there between, for example, 0.5% to 3% by weight. The active component especially when the active component is a sweetener may also be present in the edible composition in free form depending on the release profile desired.

In another aspect of the present invention, there is provided edible compositions which comprise the present delivery system and a carrier in an amount appropriate to accommodate the delivery system. The term "carrier" as used herein refers to an orally acceptable vehicle such as the soluble and insoluble components of a chewing gum composition capable of being mixed with the delivery system, and which will not cause harm to warm-blooded animals including humans. The carriers further include those components of the composition that are capable of being commingled without significant interaction with the delivery system.

In one embodiment of the present invention, the edible composition is a chewing gum composition having prolonged release (e.g., typically at least 15 minutes) of the active component. The chewing gum composition comprises a chewing gum base and the delivery system of the present invention that comprises an encapsulating material and at least one encapsulated active component such as, for example, a sweetener or a flavorant. The delivery system is present in amounts from about 0.2% to 10% by weight based on the total weight of the chewing gum composition, including 0.5, 1.0, 2.0, 3.0, 4.0, 5.0, 6.0, 7.0, 8.0, 9.0% by weight including all values and subranges there between, for example, from about 1% to 5% by weight.

The present invention may be incorporated with a variety of processes for preparing chewing gum compositions as known in the art. Such chewing gum compositions may be and include a variety of different formulations that are typically used to make chewing gum products. Typically, a chewing gum composition contains a chewable gum base portion, which is essentially free of water and is water insoluble and a water soluble bulk portion.

The water soluble portion is generally released from the gum base portion over a period of time during chewing. The gum base portion is retained in the mouth throughout the chewing. The water insoluble gum base generally comprises elastomers, elastomer solvents, plasticizers, waxes, emulsifiers, and inorganic fillers. Plastic polymers such as polyvinyl acetate, which behave somewhat as plasticizers, are also included. Other plastic polymers that may be used include polyvinyl laurate, crosslinked polyvinyl pyrrolidone and polyhydroxy alkanoates.

The elastomers may constitute from about 5% to 95% by weight of the gum base. In another embodiment, the elastomers may constitute from about 10% to 70% by weight of the gum base and in another embodiment, 15% to 45% by weight of the gum base. Examples of elastomers include synthetic elastomers such as polyisobutylene, polybutylene, isobutylene-isoprene co-polymers, styrene-butadiene co-polymers, polyvinyl acetate and the like. Elastomers may also include natural elastomers such as natural rubber as well as natural gums such as jelutong, lechi caspi, perillo, massaranduba balata, chicle, gutta hang kang or combinations thereof. Other elastomers are known to those of ordinary skill in the art.

Elastomer plasticizers modify the finished gum firmness when used in the gum base. Elastomer plasticizers are typically present in an amount up to 75% by weight of the gum base. In another embodiment, the elastomer plasticizers are present in an amount of from about 5% to 45% by weight of the gum base and in another embodiment from about 10% to 30% by weight of gum base. Examples of elastomer plasticizers include natural rosin esters such as glycerol ester of partially hydrogenated rosin, glycerol ester of tall oil rosin, pentaerythritol esters of partially hydrogenated rosin, methyl and partially hydrogenated methyl esters of rosin, and the like. Synthetic elastomer plasticizers such as terpene resins may also be employed in gum base composition.

Waxes include synthetic and naturally occurring waxes such as polyethylene, bees wax, carnauba and the like. Petroleum waxes such a paraffin may also be used. The waxes may be present in the amount up to 30% by weight of the gum base. Waxes aid in the curing of the finished gum and help improve the release of flavor and may further extend the shelf life of the product.

Elastomer solvents are often resins such as terpene resins. Plasticizers, sometimes referred to as softeners, are typically fats and oils, including tallow, hydrogenated vegetable oils, and cocoa butter.

Gum base typically also includes a filler component. The filler component modifies the texture of the gum base and aid processing. Examples of such fillers include magnesium and aluminum silicates, clay, alumina, talc, titanium oxide, cellulose polymers, and the like. Fillers are typically present in the amount of from 1% to 60% by weight.

Emulsifiers, which sometimes also have plasticizing properties, include glycerol monostearate, lecithin, and glycerol triacetate. Further, gum bases may also contain optional ingredients such as antioxidants, colors, and flavors.

The insoluble gum base may be present in the amount of from about 5% to 95% by weight of the chewing gum. In one embodiment, the insoluble gum base may present in the amount of from about 10% to 50% by weight of the gum base, and in another embodiment from about 20% to 40% by weight of the gum base.

Softeners are added to the chewing gum in order to optimize the chewability and mouth feel of the gum. Softeners, also known in the art as plasticizers or plasticizing agents, is generally present in amounts from about 0.5% to 15% by weight based on the total weight of the chewing gum composition. Softeners contemplated by the present invention include, for example, lecithin. Further, aqueous sweetener solutions such as those containing sorbitol, hydrogenated starch hydrolysate, corn syrup, and combinations thereof may be used as softeners and binding agents in the gum.

The chewing gum compositions of the present invention may be coated or uncoated and be in the form or slabs, sticks, pellets, balls and the like. The composition of the different forms of the chewing gum compositions will be similar but may vary with regard to the ratio of the ingredients. For example, coated gum compositions may contain a lower percentage of softeners. Pellets and balls have a small chewing gum core, which is then coated with either a sugar solution or a sugarless solution to create a hard shell. Slabs and sticks are usually formulated to be softer in texture than the chewing gum core.

In accordance with one aspect of the chewing gum composition of the present invention, the delivery system is added during the manufacture of the chewing gum composition. In another aspect of the present invention, the delivery system is added as one of the last steps, for example, the last step in the formation of the chewing gum composition.

The Inventors have determined that this process modification incorporates the delivery system into the gum composition without materially binding the delivery system therein such as may occur if the delivery system is mixed directly with the gum base. Thus, the delivery system, while only loosely contained within the gum composition can more effectively release the active component therefrom during a typical chewing operation. Thus, a material portion of the delivery system is free of the gum base and the corresponding ingredients of the chewing gum.

Coating techniques for applying a coating for a chewing gum composition such as pan and spray coating are well known. In one embodiment, coating with solutions adapted to build a hard candy layer can be employed. Both sugar and sugar alcohols may be used for this purpose together with high intensity sweeteners, colorants, flavorants and binders.

Other components may be added in minor amounts to the coating syrup and include moisture absorbing compounds, anti-adherent compounds, dispersing agents and film forming agents. The moisture absorbing compounds suitable for use in the coating syrups include mannitol or dicalcium phosphate. Examples of useful anti-adherent compounds, which may also function as a filler, include talc, magnesium trisilicate and calcium carbonate. These ingredients may be employed in amounts of from about 0.5% to 5% by weight of the syrup. Examples of dispersing agents, which may be employed in the coating syrup, include titanium dioxide, talc or other anti-adherent compounds as set forth above.

The coating syrup is usually heated and a portion thereof deposited on the cores. Usually a single deposition of the coating syrup is not sufficient to provide the desired amount or thickness of coating and second, third or more coats of the coating syrup may be applied to build up the weight and thickness of the coating to desired levels with layers allowed to dry in-between coats.

A method of preparing a chewing gum composition is provided by sequentially adding the various chewing gum ingredients including the delivery system of the present invention to any commercially available mixer known in the art. After the ingredients have been thoroughly mixed, the gum base is discharged from the mixer and shaped into the desired form such as by rolling into sheets and cutting into sticks, extruding into chunks, or casing into pellets.

Generally, the ingredients are mixed by first melting the gum base and adding it to the running mixer. The base may also be melted into the mixer itself. Colors or emulsifiers may also be added at this time. A softener may be added to the mixer at this time, along with syrup and a portion of the bulking agent. Further parts of the bulking agent are then added to the mixer. Flavorants are typically added with the final portion of the bulking agent. Finally, the delivery system exhibiting a predetermined tensile strength is added to the resulting mixture. Other optional ingredients are added in the batch in a typical fashion, well known to those of ordinary skill in the art.

The entire mixing procedure typically takes from five to fifteen minutes, but longer mixing times may be required. Those skilled in the art will recognize that many variations of the above-described procedure may be follows.

After the ingredients are mixed, the gum mass may be formed into a variety of shapes and products. For example, the ingredients may be formed into pellets or balls and used as cores to make a coated chewing gum product. However, any type of chewing gum product can be utilized with the present invention.

If a coated product is desired, the coating may contain ingredients such as flavorants, artificial sweeteners, dispersing agents, coloring agents, film formers and binding agents. Flavorants contemplated by the present invention, include those commonly known in the art such as essential oils, synthetic flavors, or mixtures thereof, including but are not limited to, oils derived from plants and fruits such as citrus oils, fruit essences, peppermint oil, spearmint oil, other mint oils, clove oil, oil of wintergreen, anise and the like. The flavorants may also be added to the coating syrup in an amount such that the coating may be present in amounts of from about 0.2% to 1.2% by weight flavoring agent. In another embodiment, the coating may be present in amounts from about 0.7% to 1.0% by weight flavoring agent.

Dispersing agents are often added to syrup coatings for the purpose of whitening and tack reduction. Dispersing agents contemplated by the present invention to be employed in the coating syrup include titanium dioxide, talc, or any other anti-stick compound. The dispersing agent may be added to the coating syrup in an amount such that the coating contains from about 0.1% to 1.0%, including 0.2, 0.3, 0.4, 0.5, 0.6, 0.7, 0.8, 0.9 and all values and ranges there between, for example, from about 0.3% to 0.6% by weight of the agent.

Coloring agents may be added directly to the coating syrup in dye or lake form. Coloring agents contemplated by the present invention include food quality dyes. Film formers may be added to the coating syrup include methylcellulose, carboxymethyl cellulose, ethyl cellulose, hydroxyethyl cellulose, and the like or combinations thereof. Binding agents may be added either as an initial coating on the chewing gum center or may be added directly to the coating syrup. Binding agents contemplated by the present invention include gum arabic, gum talha, gelatin, vegetable gums, and the like. The binding agents, when added to the coating syrup, are typically added in amounts from about 0.5% to 10% by weight.

The present invention further encompasses confectionery compositions containing the delivery system of the present invention. Confectionery compositions include, for example, compressed tablets such as mints, hard boiled candies, chocolates, chocolate containing products, nutrient bars, nougats, gels, centerfill confections, fondants, panning goods, consumable thin films and other compositions falling within the generally accepted definition of confectionery compositions.

Confectionery compositions in the form of pressed tablets such as mints may generally be made by combining finely sifted sugar or sugar substitute, flavoring agent (e.g. peppermint flavor) bulking agent such as gum arabic, and an optional coloring agent. The flavoring agent, bulking agent are combined and then gradually the sugar or sugar substitute are added along with a coloring agent if needed.

The product is then granulated by passing through a seize of desired mesh size (e.g. 12 mesh) and then dried typically at temperatures of from about 55° C. to 60° C. The resulting powder is fed into a tableting machine fitted with a large size punch and the resulting pellets are broken into granules and then pressed.

High boiled candies typically contain sugar or sugar substitute, glucose, water, flavoring agent and optional coloring agent. The sugar is dissolved in the water and glucose is then added. The mixture is brought to a boil. The resulting liquid to which may previously have been added a coloring agent is poured onto an oiled slab and cooled. The flavoring agent are then added and kneaded into the cooled mass. The resulting mixture is then fed to a drop roller assembly known in the art to form the final hard candy shape.

A nougat composition typically includes two principal components, a high boiled candy and a frappe. By way of example, egg albumen or substitute thereof is combined with water and whisked to form a light foam. Sugar and glucose are added to water and boiled typically at temperatures of from about 130° C. to 140° C. and the resulting boiled product is poured into a mixing machine and beat until creamy.

The beaten albumen and flavoring agent are combined with the creamy product and the combination is thereafter thoroughly mixed.

Further details regarding the preparation of confectionery compositions can be found in Skuse's Complete Confectioner (13$^{th}$ Edition) (1957) including pp. 41-71, 133-144, and 255-262; and Sugar Confectionery Manufacture (2$^{nd}$ Edition) (1995), E. B. Jackson, Editor, pp. 129-168, 169-188, 189-216, 218-234, and 236-258 each of which is incorporated herein by reference.

Except as otherwise noted, the amount of the ingredients incorporated into the compositions according to the present invention is designated as % by weight based on the total weight of the composition.

EXAMPLES

Example 1

Encapsulation of Aspartame-Polyvinylacetate Matrix (Aspartame 30%)

The following composition is prepared:

| Ingredient | Percent |
| --- | --- |
| Polyvinyl Acetate | 65.00% |
| Hydrogenated Oil | 3.75% |
| Glycerol Monostearate | 1.25% |
| Aspartame | 30.00% |
| Total | 100.00% |

Polyvinylacetate is melted at a temperature of about 110° C. in a high shear mixer such as extruder (single or twin screw) or sigma or Banbury mixer. The hydrogenated oil and Glycerol monostearate are then added to the molten polyvinylacetate. Aspartame is then added to the resulting mixture and mixed under high shear to completely disperse the ingredients. The resulting filled polymer melt is cooled and ground to particle size of less than 420 microns. The encapsulated Aspartame matrix is stored in air tight containers with low humidity below 35° C.

Example 2

Encapsulation of AceK—Polyvinylacetate Matrix (AceK 30%)

The following composition is prepared:

| Ingredient | Percent |
| --- | --- |
| Polyvinyl Acetate | 65.00% |
| Hydrogenated Oil | 3.75% |
| Glycerol Monostearate | 1.25% |
| AceK | 30.00% |
| Total | 100.00% |

Polyvinylacetate is melted at a temperature of about 110° C. in a high shear mixer such as extruder (single or twin screw) or sigma or Banbury mixer. The hydrogenated oil and Glycerol monostearate are then added to the molten polyvinylacetate. AceK is then added to the resulting mixture and mixed under high shear to completely disperse the ingredients. The resulting filled polymer melt is cooled and ground to particle size of less than 420 microns. The encapsulated AceK matrix is stored in air tight containers with low humidity below 35° C.

Example 3

Encapsulation of Mixed Aspartame and AceK-Polyvinylacetate Matrix (Actives=30%)

The following composition is prepared:

| Ingredient | Percent |
| --- | --- |
| Polyvinyl Acetate | 65.00% |
| Hydrogenated Oil | 3.75% |
| Glycerol Monostearate | 1.25% |
| Aspartame | 21.00% |
| AceK | 9.00% |
| Total | 100.00% |

Polyvinylacetate is melted at a temperature of about 110° C. in a high shear mixer such as extruder (single or twin screw) or sigma or Banbury mixer. The hydrogenated oil and Glycerol monostearate are then added to the molten polyvinylacetate. Aspartame and AceK (60/40) are then added to the resulting mixture and mixed under high shear to completely disperse the ingredients. The resulting filled polymer melt is cooled and ground to particle size of less than 420 microns. The mixed Aspartame and AceK encapsulation matrix is stored in air tight containers with low humidity below 35° C.

Example 4

Chewing Gum Composition Containing LL Aspartame and AceK Encapsulated Individually The following chewing gum is prepared:

| Ingredient | Percent |
| --- | --- |
| Gum Base | 39.00 |
| Sorbitol | 44.30 |
| Mannitol | 9.00 |
| Flavor | 3.67 |
| Glycerin | 1.50 |
| Lecithin | 0.20 |
| LL encapsulated aspartame from example 1 (30% active) | 1.63 |
| LL encapsulated AceK from example 2 (30% active) | 0.70 |
| Total | 100.00 |

Gum is prepared in the following manner: The gum base is melted in a mixer. The remaining ingredients are added to the molten gum base. The melted gum base with ingredients are mixed to completely disperse the ingredients. The resulting chewing gum is allowed to cool. The cooled chewing gum is sized and conditioned for about a week and packaged.

Example 5

Chewing Gum Composition Containing LL Aspartame and AceK (Mixed) Encapsulated The following chewing gum is prepared:

| Ingredient | Percent |
|---|---|
| Gum Base | 39.00 |
| Sorbitol | 44.30 |
| Mannitol | 9.00 |
| Flavor | 3.67 |
| Glycerin | 1.50 |
| Lecithin | 0.20 |
| LL encapsulated APM + AceK from example 3 (30% active) | 2.33 |
| Total | 100.00 |

Gum is prepared in the following manner: The gum base is melted in a mixer. The remaining ingredients are added to the molten gum base. The melted gum base with ingredients are mixed to completely disperse the ingredients. The resulting chewing gum is allowed to cool. The cooled chewing gum is sized and conditioned for about a week and packaged.

Chew-out release studies are conducted and show that the chewing gum prepared in Example 5 containing mixed aspartame and aceK encapsulations exhibited significantly improved release profiles compared to the chewing gum prepared in Example 4, which contained a mixture of aspartame and aceK separately encapsulated.

Obviously, numerous modifications and variations of the present invention are possible in light of the above teachings. It is therefore to be understood that within the scope of the appended claims, the invention may be practiced otherwise than as specifically described herein.

The invention claimed is:

1. A delivery system for inclusion in an edible composition comprising two or more active components, at least one encapsulating material selected from the group consisting of polyvinyl acetate, crosslinked polyvinyl pyrrolidone, polylactic acid, polyhydroxyalkanoates, and combinations thereof, and a tensile strength modifying agent selected from the group consisting of hydrogenated vegetable oil, talc, dicalcium phosphate, calcium carbonate and combinations thereof; wherein the two or more active components are present in the delivery system such that the two or more active components are released from an edible composition comprising the delivery system when consumed in a similar or substantially similar amount compared to the two or more active components added to the delivery system relative to the amount of the two or more active components released from an edible composition comprising separate delivery systems of each of the two or more active components; wherein the amount of the two or more active components is from about 1% to about 70% by weight of the total weight of the delivery system; wherein the amount of encapsulating material is about 30% to about 99% by weight of the total weight of the delivery system; wherein the amount of the tensile strength modifying agent is 1% to 40% by weight of the total weight of the delivery system; and wherein the delivery system has a tensile strength of at least 10,000 psi.

2. The delivery system of claim 1, wherein the two or more active components are released from the edible composition for at least 10 minutes.

3. The delivery system of claim 1, wherein the two or more active components are released from the edible composition for at least 20 minutes.

4. The delivery system of claim 1, wherein the two or more active components are released from the edible composition for at least 30 minutes.

5. The delivery system of claim 1, which has a tensile strength of at least 20,000 psi.

6. The delivery system of claim 1, wherein the two or more active components are selected from the group consisting of a sweetener, an acid, a flavorant, a pharmaceutical, a therapeutic agent, a vitamin, a breath freshener, a cooling agent and combinations thereof.

7. The delivery system of claim 6, wherein at least one of the two or more active components is a sweetener.

8. The delivery system of claim 7, wherein the sweetener is a high intensity sweetener.

9. The delivery system of claim 6, wherein at least two of the two or more active components are sweeteners.

10. The delivery system of claim 9, wherein the sweeteners are high intensity sweeteners.

11. The delivery system of claim 6, wherein the one or more of the active components is a sweetener selected from the group consisting of an amino acid based sweetener, a dipeptide sweetener, glycyrrhizin, saccharin, a saccharin salt, an acesulfame salt, a cyclamate, a stevioside, talin, a dihydrochalcone compound, a chlorinated sucrose, and combinations thereof.

12. The delivery system of claim 6, wherein one or more of the active components is a sweetener selected from the group consisting of neotame, aspartame, sucralose, acesulfame potassium, and a mixture thereof.

13. The delivery system of claim 12, wherein one sweetener is aspartame and a second sweetener is acesulfame potassium.

14. An edible composition comprising at least one delivery system of claim 1.

15. The edible composition of claim 14, which is selected from the group consisting of a food product, a pharmaceutical composition, a foodstuff, a nutrient-containing composition, a vitamin, a nutraceutical, and a combination thereof.

16. The edible composition of claim 15, which is a chewing gum, wherein the delivery system is present in an amount from about 0.2% to about 10% by weight based on the total weight of the chewing gum.

17. A method of managing the release profile of at least two active components from at least one delivery system suitable for incorporation into an edible composition, comprising
   selecting a desired release profile of the at least two active components, wherein the delivery system comprises at least one encapsulating material wherein the encapsulating material is selected from the group consisting of polyvinyl acetate, crosslinked polyvinyl pyrrolidone, polylactic acid, polyhydroxyalkanoates, and combinations thereof, the at least two active components, and at least one tensile strength modifying agent selected from the group consisting of hydrogenated vegetable oil, talc, dicalcium phosphate, calcium carbonate, and combinations thereof; and
   selecting amounts of the at least two active components, the at least one encapsulating material, and the at least one tensile strength modifier such that the delivery of the at least two active components are released at the desired release profile selected when the delivery system is incorporated into the edible composition; wherein the amount of the at least two active components is about 1% to about 70% by weight based on the total weight of the delivery system; wherein the amount of the at least one encapsulating material is about 30% to about 99% by weight of the total delivery system; and the amount of the tensile strength modifying agent is from 1% to 40% by weight of the total delivery system; and wherein the delivery system has a tensile strength of at least 10,000 psi; an average particle size of 75 to 900 microns; and wherein the delivery system is present in an amount from about 0.2% to about 10% by weight based on the total weight of the edible material.

18. The method of claim 17, wherein at least one active component is a sweetener.

19. The method of claim 17, wherein at least two active components are sweeteners.

20. A delivery system for inclusion in a chewing gum composition comprising two active components, wherein one active component is aspartame and the second active component is acesulfame potassium, at least one encapsulating material, wherein the at least one encapsulating material is selected from the group consisting of polyvinyl acetate, crosslinked polyvinyl pyrrolidone, polylactic acid, polyhydroxyalkanoates, and combinations thereof; and at least one tensile strength modifying agent, wherein the at least one tensile strength modifying agent is one or more hydrogenated vegetable oils; wherein the two or more active components are present in the delivery system such that the two or more active components are released from an edible composition comprising the delivery system when consumed in a similar or substantially similar amount compared to the two or more active components added to the delivery system relative to the amount of the two or more active components released from an edible composition comprising separate delivery systems of each of the two or more actives; wherein the amount of the two or more active components is about 10% to about 40% based on the total amount of the delivery system; wherein the amount of the at least one encapsulating material is about 60% to about 90% by weight of the total weight of the delivery system; wherein the amount of the at least one tensile strength modifying agent is 1% to 5%; and wherein the delivery system has a tensile strength of at least 10,000 psi and has an average particle size from about 75 microns to about 900 microns.

21. An chewing gum composition comprising at least one delivery system of claim 20; wherein the delivery system is present in an amount from about 0.2% to about 10% by weight based on the total weight of the chewing gum composition.

22. The delivery system of claim 1, wherein the tensile strength modifying agent comprises one or more hydrogenated vegetable oils and the amount of the one or more hydrogenated vegetable oils is from 1% to 5% by weight based on the total weight of the delivery system.

23. The delivery system of claim 1, wherein the at least one encapsulating material comprises polyvinyl acetate, and wherein the tensile strength modifying agent comprises one or more hydrogenated vegetable oils and the amount of the one or more hydrogenated vegetable oils is from 1% to 5% by weight based on the total weight of the delivery system.

24. The method of claim 17, wherein the at least one tensile strength modifier modifying agent comprises one or more hydrogenated vegetable oil and the amount of the one or more hydrogenated vegetable oil is from 1% to 5% by weight based on the total weight of the delivery system.

25. The method of claim 17, wherein the at least one encapsulating material comprises polyvinyl acetate, and wherein the at least one tensile strength modifying agent comprises one or more hydrogenated vegetable oils and the amount of the one or more hydrogenated vegetable oil is from 1% to 5% by weight based on the total weight of the delivery system.

26. The delivery system of claim 20, wherein the at least one encapsulating material comprises polyvinyl acetate, and wherein the tensile strength modifying agent comprises one hydrogenated vegetable oil.

27. A method for preparing an edible composition containing a delivery system useful for delivering at least two active components at a desired release profile, said method comprising the steps:

(1) combining at least two active components, at least one encapsulating material, and at least one tensile strength modifying agent; wherein the encapsulating material is selected from the group consisting of polyvinyl acetate, crosslinked polyvinyl pyrrolidone, polylactic acid, polyhydroxyalkanoates, and combinations thereof; wherein the tensile strength modifying agent selected from the group consisting of hydrogenated vegetable oil, talc, dicalcium phosphate, calcium carbonate, and combinations thereof to at least partially encapsulate the at least two active components in the at least one encapsulating material and thereby form a delivery system; wherein the amount of the two or more active components is from about 1% to about 70% by weight based on the total weight of the delivery system; wherein the amount of the at least one encapsulating material is from about 30% to about 99% by weight based on the total weight of the delivery system; wherein the amount of the at least one tensile strength modifying agent is 1% to 40% by weight based on the total weight of the delivery system; and wherein the delivery system has a tensile strength of at least 10,000 psi;

(2) grinding the delivery system to an average particle size of about 75 microns to about 900 microns; and (3) adding the delivery system to an edible product.

28. The method of claim 27 wherein said edible product is chewing gum; wherein the delivery system is present in an amount from about 0.2% to about 10% by weight based on the total weight of the chewing gum composition.

29. The method of claim 27 wherein the tensile strength modifying agent is one or more hydrogenated vegetable oils present in an amount from 1% to 5% by weight based on the total weight of the delivery system.

* * * * *